US008097774B2

(12) United States Patent
Hawkes et al.

(10) Patent No.: US 8,097,774 B2
(45) Date of Patent: Jan. 17, 2012

(54) CYTOCHROME P450 GENES CONFERRING HERBICIDE RESISTANCE

(75) Inventors: Timothy Robert Hawkes, Bracknell (GB); Bernardus Theodorus Maria Vernooij, Durham, NC (US)

(73) Assignee: Syngenta Participations AG, Basel (CH)

( * ) Notice: Subject to any disclaimer, the term of this patent is extended or adjusted under 35 U.S.C. 154(b) by 486 days.

(21) Appl. No.: 12/156,247

(22) Filed: May 30, 2008

(65) Prior Publication Data

US 2009/0011936 A1 Jan. 8, 2009

Related U.S. Application Data

(60) Provisional application No. 60/932,560, filed on May 30, 2007.

(51) Int. Cl.
*C12N 15/82* (2006.01)
(52) U.S. Cl. ...................................................... 800/300
(58) Field of Classification Search .................... None
See application file for complete search history.

(56) References Cited

U.S. PATENT DOCUMENTS

| | | | |
|---|---|---|---|
| 4,780,127 A | 10/1988 | Michaely et al. | |
| 5,006,158 A | 4/1991 | Carter et al. | |
| 5,349,127 A | 9/1994 | Dean | |
| 5,656,573 A | 8/1997 | Roberts et al. | |
| 5,882,851 A | 3/1999 | Koch | |
| 6,121,512 A | 9/2000 | Siminszky | |
| 6,300,544 B1 | 10/2001 | Halkier | |
| 6,367,429 B2 | 4/2002 | Van Almsick et al. | |
| 6,380,465 B1 | 4/2002 | Barrett | |
| 6,534,444 B1 | 3/2003 | Sievernich et al. | |
| 6,649,814 B2 | 11/2003 | Halkier et al. | |
| 6,844,294 B2 | 1/2005 | Auler et al. | |
| 7,005,283 B2 | 2/2006 | Croteau | |
| 7,250,561 B1 * | 7/2007 | Pallett et al. ............ | 800/300 |
| 7,405,057 B2 | 7/2008 | Chappell | |
| 7,608,564 B2 | 10/2009 | Von Deyn et al. | |
| 7,705,200 B2 * | 4/2010 | Dam et al. ............... | 800/278 |
| 2004/0034888 A1 | 2/2004 | Liu et al. | |
| 2004/0058427 A1 | 3/2004 | Andrews | |
| 2005/0060767 A1 | 3/2005 | Subramanian et al. | |
| 2005/0204436 A1 | 9/2005 | Hammer | |
| 2005/0246800 A1 | 11/2005 | Dunne et al. | |
| 2006/0117406 A1 | 6/2006 | Schultze | |
| 2007/0079393 A1 | 4/2007 | McCutchen et al. | |
| 2007/0214515 A1 | 9/2007 | Dam | |

FOREIGN PATENT DOCUMENTS

| | | |
|---|---|---|
| AU | 199958616 | 5/2000 |
| AU | 755314 B2 | 12/2002 |
| EP | 1728868 | 12/2006 |
| WO | 98/20144 A2 | 5/1998 |
| WO | WO 98/31681 | 7/1998 |
| WO | WO 99/65314 | 12/1999 |
| WO | WO 00/15615 | 3/2000 |
| WO | WO 00/21924 | 4/2000 |
| WO | 02/46387 A2 | 6/2002 |
| WO | WO 02/085118 | 10/2002 |
| WO | 2007/000077 A1 | 1/2007 |
| WO | 2007/024739 A2 | 3/2007 |
| WO | WO 2007/103567 | 9/2007 |

OTHER PUBLICATIONS

Pan et al, Aug. 2006, Plant Molecular Biology 61: 933-943.*
Frear, D.S. et al "N-demethylation of substituted 3-(phenyl)-1-methylureas: isolation and characterization of a microsomal mixed function oxidase from cotton", *Phytochemistry* (1969) 8: 2157-2169.
Grossmann, Klaus et al "On the mechanism of action and selectivity of the corn herbicide topramezone: a new inhibitor of 4-hydroxyphenylpyruvate dioxygenase" *Pest Mgmt. Sci.* (2007) 63:429-439.
Hawkes et al. "Mesotrione: Mechanism of herbicidal activity and selectivity in corn", *Proc. Brighton Pest Cont Conf-Weeds*, BCPC, (2001) 563-568.
Shiota et al. "Herbicide-resistant tobacco plants expressing the fused enzyme between rat cytochrome P4501A1 (CYP1A1) and yeast NADPH-cytochrome P450 oxidoreductase", *Plant Physiol.* (1994) 106:17-23.
Siminszky et al. "Expression of a soybean cytochrome P450 monooxygenase cDNA in yeast and tobacco enhances the metabolism of phenylurea herbicides", *Proc. Natl. Acad. Sci USA* (1999) 96:1750-1755.
Bolwell et al (1994) Phytochemistry 37: 1491-1506.
Mizutani and Ohta (1998) Plant Physiol., 116, 357-367.
Morant et al. (2003) Current Opinion in Biotechnology, 14:151-162.
Robineau et al. (1998) Plant Physiol., 118:1049-1056.
Didierjean et al. (2002) Plant Physiol. 130:179-189.
Persans et al (2001) Plant physiol., 125:1126-1138.
Shuler (1996) Crit. Rev. Plant. Sci, 15:235-284.
Pan et al. (2006) Plant Molecular Biology, 61:933-943.

(Continued)

*Primary Examiner* — David H Kruse
(74) *Attorney, Agent, or Firm* — S. Matthew Edwards

(57) ABSTRACT

Compositions and methods for conferring herbicide resistance or tolerance to plants, plant cells, tissues and seeds are provided. Compositions include transgenic plants, plant cells, tissues, and seeds that have been transformed with a nucleic acid molecule encoding a cytochrome P450 or variant thereof that confers herbicide resistance or tolerance, alone or in combination with one or more additional nucleic acid molecules encoding polypeptides that confer desirable traits. In particular, the cytochrome P450 or variant thereof confers resistance or tolerance to HPPD inhibitors, benzothiadiazinones, sulfonylureas, and other classes of herbicides. The additional polypeptide may also confer resistance or tolerance to an herbicide, including HPPD inhibitors and other herbicides. Methods are also provided for the production and use of the herbicide resistant or tolerant plants, plant cells, tissues and seeds of the invention.

7 Claims, 4 Drawing Sheets

OTHER PUBLICATIONS

Siminszky (2006) Phytochemistry Reviews, 5:445-458.
Werck-Reichhart et al. (2000) Trends in Plant Science, 5:116-123.
Ohkawa et al. (1999) Pesticide Science, 55:867-874.
Kreuz et al. (1996) Plant Physiology, 111:349-353.
O'Keefe et al. (1994) Plant Physiology, 105:473-482.
Williams et al., Map-based cloning of the nsf1 (nicosulfuron susceptible 1) gene of maize, P26, 48th Annual Maize Genetics Conference, Mar. 9-12, 2006, Asiolmar Conference Grounds, Pacific Grove, California.
Williams et al. (2005) HortScience, 40:1801-1805.
Hawkes et al., Mesotrione: Mechanism of herbicidal activity and selectivity in corn, The BCPC Conference—Weeds 2001, Brighton Metropole Hotel, Brighton, UK, Nov. 12-15, 2001.
Armel. Weed management in conventional, no-till, and transgenic corn with mesotrione combinations and other herbicides. PhD Dissertation (Chapter 1) Apr. 29, 2002.
Bierman et al Fungicide-herbicide interaction in soybean (*Glycine max*). *Crop Protection* 25 (2006)134-139.
Frear, et al "Metabolism of flumetsulam (DE-498) in wheat, corn, and barley" *Pesticide biochemistry and physiology* (USA) Mar. 1993, 45(3): 178-192; Abstract.
Gang, Pan et al "Map-based cloning of a novel rice cytochrome P450 gene CYP81A6 that confers resistance to two different classes of herbicides" *Plant Molecular Biology*, Aug. 1, 2006, vol. 61, No. 6, pp. 933-943.
Kawahigashi et al "Broad range of herbicide tolerance of glutinous upland rice variety 'Yumenohatamochi' carrying human cytochrome P450 genes" *Plant Biotechnology*, 23:227-231; p. 229 (2006).
Kawahigashi et al "Herbicide resistance of transgenic rice plants expressing human CYP1A1" *Biotechnology Advances*, 25 (2007) 75-84; abstract.
Letouze et al Inheritance of fenoxaprop-P-ethyl resistance in blackgrass (*Alopecurus myosuroides* Huds.) population. *Theor Appl Genet*, 2001, 103:288-296.
Matringe et al, "p-Hydroxyphenylpyruvate dioxygenase inhibitor-resistant plants" *Pest Management Science*, 2005, 61: 269-276.
Subramanian et al "Engineering dicamba selectivity in crops: a search for appropriate degradative enzyme(s)." *Journal of Industrial Microbiology & Biotechnology*, 1997, 19:344-349; abstract.
Search Report dated Jun. 10, 2009 issued in corresponding International Application No. PCT/US2008/006891.

* cited by examiner

Figure 2

| Sequence Identification Number | Sequence |
|---|---|
| SEQ ID NO:1 | Maize nsf1 CYP amino acid sequence, deduced from the nsf1 gene sequence derived from B73 BAC clone b0159B4 |
| SEQ ID NO:2 | Optimized nsf1 gene sequence |
| SEQ ID NO:3 | Maize CYP72A1 amino acid sequence |
| SEQ ID NO:4 | Optimized CYP72A1 gene sequence |
| SEQ ID NO:5 | Rice CYP81A6 amino acid sequence, G. Pan *et al.* (2007) *Plant Mol. Biol.*, 61:933-943; GenBank accession no: ABC69856 |
| SEQ ID NO:6 | Optimized CYP81A6 gene |
| SEQ ID NO:7 | Amino acid sequence from gene 160842 (derived from corn line SSCIC008) |
| SEQ ID NO:8 | Amino acid sequence from gene 136090 (derived from corn line B73, BAC b0159B4) |
| SEQ ID NO:9 | Catharanthus CP72A1 amino acid sequence (Persans *et al.* (2001) *Plant Physiol.*, 125:1126); Genbank Accession: AAA33106 |
| SEQ ID NO:10 | Avena HPPD amino acid sequence |
| SEQ ID NO:11 | Modified Avena HPPD amino acid sequence |
| SEQ ID NO:12 | Modified Avena HPPD amino acid sequence |
| SEQ ID NO:13 | Modified Avena HPPD amino acid sequence |
| SEQ ID NO:14 | Synthetic, optimized Avena HPPD gene sequence |
| SEQ ID NO:15 | Synthetic, optimized, modified Avena HPPD gene sequence |

# CYTOCHROME P450 GENES CONFERRING HERBICIDE RESISTANCE

FIELD OF THE INVENTION

The present invention relates to herbicide tolerant plants and the use of herbicides over such plants. More particularly, the present invention relates to genes for the production of commercial plants that are resistant to certain classes of herbicides that inhibit hydroxyphenyl pyruvate dioxygenase (HPPD) as well other classes of herbicides. Specifically, the present invention relates to the degradation of such herbicides in plants by expression of certain cytochrome P450 genes.

BACKGROUND OF THE INVENTION

Cytochrome P450 (P450) monooxygenases are ubiquitous hemoproteins present in microorganisms, plants and animals. Comprised of a large and diverse group of isozymes, P450s mediate a great array of oxidative reactions using a wide range of compounds as substrates, and including reactions involved in biosynthetic processes such as phenylpropanoid, fatty acid, and terpenoid biosynthesis; metabolism of natural products; and detoxification of foreign substances (xenobiotics). See e.g., Schuler (1996) *Crit. Rev. Plant Sci.* 15:235-284 (1996). In a typical P450 catalyzed reaction, one atom of molecular oxygen ($O_2$) is incorporated into the substrate, and the other atom is reduced to water. Electrons are supplied through oxidation of NADPH. For most eukaryotic P450s, NADPH:cytochrome P450 reductase, a membrane-bound flavoprotein, transfers the necessary two electrons from NADPH to the cytochrome P450 (Bolwell et al (1994) *Phytochemistry* 37: 1491-1506; Mizutani and Ohta (1998) *Plant Physiol.*, 16, 357-367).

Plant cytochrome P450s are known to be involved in the metabolism and detoxification of numerous pesticides as well as in the biosynthesis of primary and secondary metabolites. Much of the evidence has been gathered via traditional chemistry techniques (Shuler (1996) *Crit. Rev. Plant. Sci.* 15:235-284; Bolwell et al. (1994) *Phytochemistry* 37:1491-1506; Frear et al. (1969) *Phytochemistry* 8:2157-2169) and through studies of mammalian or bacterial genes in plants (Shiota et al. (1994) *Plant Physiol.* 106:17-23; O'Keefe et al. (1994) *Plant Physiol.* 105:473-482).

Recently, endogenous plant P450s have been successfully cloned, expressed, characterised and assayed in heterologous systems (Siminszky et al. (1999) PNAS (USA) 96:1750-1755). For example, CYP76B1 was cloned (Robineau et al. (1998) *Plant Physiol.*, 118:1049-1056) from the Jerusalem artichoke (*Helianthus tuberosus*). This xenobiotic inducible cytochrome P450 was found to be strongly inducible and to catalyze the rapid oxidative N-dealkylation of various phenylurea herbicides to yield non-phytotoxic metabolites. Heterologous expression of the CYP76B1 gene in tobacco (*Nicotiana tabacum*) and *Arabidopsis* resulted in increased rates of herbicide oxidation and was, by itself, sufficient to yield a 20 fold level of tolerance to linuron, a compound detoxified by a single dealkylation, and also a 10-fold increase in tolerance to isoproturon or chlortoluron, which need successive catalytic steps for detoxification (Didierjean et al. (2002) *Plant Physiol.* 130:179-189).

Frear et al. (1969) *Phytochemistry* 8:2157-2169 demonstrated the metabolism of monuron by a mixed-function oxidase located in a microsomal fraction of cotton seedlings. Further evidence has accumulated supporting the involvement of P450s in the metabolism and detoxification of numerous herbicides representing several distinct classes of compounds (reviewed in Bolwell et al. (1994) *Phytochemistry* 37:1491-1506; Shuler (1996) *Crit. Rev. Plant. Sci.* 15:235-284). Likewise, the crop/weed selectivity of certain HPPD-inhibiting herbicides such as mesotrione (Hawkes et al. (2001) *Proc. Brighton Pest Cont Conf-Weeds*, BCPC, 563-568) and topramezone (Grossmann and Ehrhardt (2007) *Pest Mgmt. Sci.* 63:429-439) for example is largely dependent on the activity of cytochrome P450 type enzymes.

Differential herbicide metabolizing P450 activities are believed to represent one of the mechanisms that enable certain crop species to be more tolerant of a particular herbicide than other crop or weedy species. The following patents and applications collect information useful for the background understanding of cytochrome P450 use for herbicide tolerance (U.S. Pat. Nos. 6,380,465; 6,121,512; 5,349,127; and PCT Patent App. Pub. No. WO2007000077). See also U.S. Pat. Nos. 6,649,814 and 6,300,544 for disclosure relating to cytochrome P450 monooxygenases for obtaining transgenic plants resistant to insects, acarids, or nematodes, or with improved nutritive value.

Methods for providing plants which are tolerant to HPPD herbicides which comprise transformation of plant material with polynucleotides comprising regions which encode HPPD enzymes are known (See, e.g., U.S. Application Publication Number 2004/0058427; PCT application WO98/20144; PCT application WO 02/46387; see also U.S. Application Publication Number 2005/0246800 relating to identification and labelling of soybean varieties as being relatively HPPD tolerant). However what has not hitherto been generally recognised is that cytochrome P450 enzymes can provide additional or commercial levels of tolerance to HPPD-inhibitor and other herbicides, when expressed either in combination with HPPD enzymes, or in tolerant backgrounds, or alone in a transformed plant. While a given HPPD enzyme may provide a useful level of tolerance to some HPPD-inhibitor herbicides it may be quite inadequate to provide commercial levels of tolerance to a different, more desirable HPPD-inhibitor herbicide which, for example, may control a different spectrum of weeds, be cheaper to make or offer environmental benefits. As well as particular HPPD enzymes and the polynucleotides which encode them the current invention provides a means of enhancing the effect of HPPD enzymes suitable for providing commercially useful levels of resistance to particular HPPD-inhibitor herbicide chemistries through the use of cytochrome P450 enzymes that degrade certain, below-specified, HPPD-inhibitor herbicide chemistries. In addition, expression of these cytochrome P450 enzymes also provides a means of reducing the amount of parent active herbicide that persists in plant tissues and of therefore decreasing the overall amount of parent herbicide residue entering the food and feed chain as a result of application to food or feed crops.

In addition, the genes disclosed herein also provide an alternative process for providing resistance to various xenobiotics including herbicides and including some types, such as sulfonylureas having a non-HPPD mode of action.

SUMMARY OF THE INVENTION

Compositions and methods for conferring herbicide resistance or tolerance to plants, plant cells, tissues and seeds are provided. Compositions include transgenic plants, plant cells, tissues, and seeds that have been transformed with a nucleic acid molecule encoding a cytochrome P450 or variant thereof that confers herbicide resistance or tolerance, alone or in combination with one or more additional nucleic acid molecules encoding polypeptides that confer desirable traits.

In particular, the cytochrome P450 or variant thereof confers resistance or tolerance to HPPD inhibitors, Benzothiadiazinones, Sulfonylureas, and other classes of herbicides including, for example, Imidazolinones, Triazolopyrimidines, Pyrimidinylthiobenzoates, Triazolinones, Auxins, Acetyl-coenzyme A Carboxylase (ACCase) inhibitors, Photosystem II (PSII) inhibitors, Protoporphyrinogen Oxidase (PPO) inhibitors, Phytoene Desaturase (PDS) inhibitors, Dinitroanalines, and Acetamides, as well as herbicides with unknown modes of action such as Difenzoquat and Clomazone. The additional polypeptide may also confer resistance or tolerance to an herbicide, including HPPD inhibitors and other herbicides. Methods are also provided for the production and use of the herbicide resistant or tolerant plants, plant cells, tissues and seeds of the invention.

The present invention provides gene sequences set forth in SEQ ID NOS:2, 4, and 6, that encode cytochrome P450 enzymes capable of degrading certain herbicides of the HPPD classes of herbicides when expressed in plants. The present invention also relates to transformed plants overexpressing the P450s set forth in SEQ ID NOS:1, 3, and 5, genetic constructs for overexpressing the genes in plants, and to the over-the-top application of HPPD class herbicides, both alone and in combination with other herbicides, to HPPD resistant plants, especially crop plants in fields, for weed control without damage to the crop plants. The present invention also contemplates combining the P450 genes in the same plant with genes conferring resistance to other herbicides, for example EPSPS genes (for instance, EPSPS genes with natural tolerance to glyphosate) conferring resistance to glyphosate, and phosphinothricin acetyl transferase genes (PAT and BAR genes, described in U.S. Pat. Nos. 5,561,236 and 5,276,268) conferring resistance to glufosinate. Furthermore, the present invention also provides plants with reduced HPPD herbicide residue levels.

BRIEF DESCRIPTION OF THE FIGURES

FIG. 2 shows a list of polynucleotide and amino acid sequences relating to cytochrome P450 enzymes for use in the present invention.

DETAILED DESCRIPTION

Overview

Figure 1:
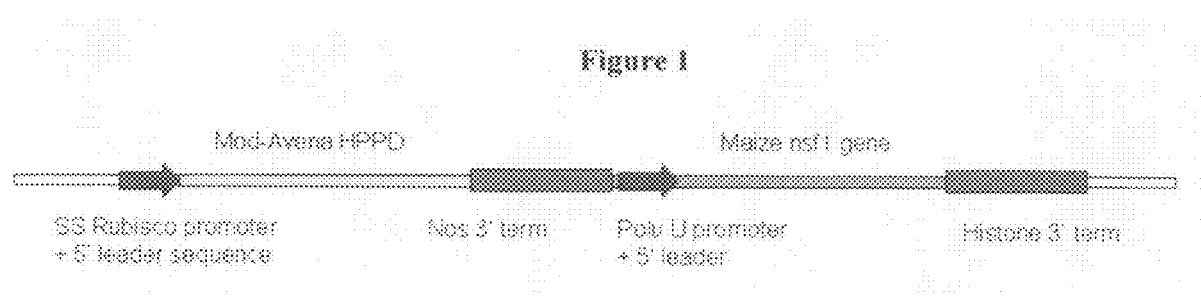
FIG. 1 shows a DNA construct comprising: 1) a cassette having a modified *Avena* HPPD gene under operable expression control of an upstream promoter (e.g., a small subunit of Rubisco promoter region including 5' untranslated leader sequence) and a downstream nopaline synthase 3' terminator sequence; 2) a DNA sequence encoding the maize nsf1 protein sequence (SEQ ID NO:2) under operable control of an upstream *Arabidopsis* or soybean polyubiquitin promoter and 5' untranslated leader sequence and a downstream 3' terminator sequence from a histone gene.

The present invention relates to recombinant DNA technology, and in particular to the production of: (i) transgenic plants which exhibit substantial resistance or substantial tolerance to herbicides when compared with non-transgenic-like plants; and (ii) transgenic plants having an enhanced ability to transform certain herbicides to oxidised metabolites, when likewise compared with such non-transgenic-like plants. The invention also relates, inter alia, to the nucleotide sequences (and expression products thereof) when used in the production of, or when produced by, the said transgenic plants. Compositions of the invention include transgenic plants, plant cells, tissues, and seeds that have been transformed with a nucleic acid molecule encoding a cytochrome P450 or variant thereof that confers herbicide resistance or tolerance, alone or in combination with one or more additional nucleic acid molecules encoding polypeptides that confer desirable traits. In particular, the cytochrome P450 or variant thereof confers resistance or tolerance to HPPD inhibitors, Benzothiadiazinones, Sulfonylureas, and other classes of herbicides including, for example, Imidazolinones, Triazolopyrimidines, Pyrimidinylthiobenzoates, Triazolinones, Auxins, Acetyl-coenzyme A Carboxylase (ACCase) inhibitors, Photosystem II (PSII) inhibitors, Protoporphyrinogen Oxidase (PPO) inhibitors, Phytoene Desaturase (PDS) inhibitors, Dinitroanalines, and Acetamides, as well as herbicides with unknown modes of action such as Difenzoquat and Clomazone. The additional polypeptide may also confer resistance or tolerance to an herbicide, including HPPD inhibitors and other herbicides. Methods are also provided for the production and use of the herbicide resistant or tolerant plants, plant cells, tissues and seeds of the invention.

Within the context of the present invention the terms hydroxy phenyl pyruvate (or pyruvic acid) dioxygenase (HPPD), 4-hydroxy phenyl pyruvate (or pyruvic acid) dioxygenase (4-HPPD) and p-hydroxy phenyl pyruvate (or pyruvic acid) dioxygenase (p-HPPD) are synonymous.

As used herein, plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill or damage", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agricultural community to kill weeds in the field.

As used herein, "non-trangenic-like plants" are plants that are similar or the same as transgenic plants but that do not contain a transgene conferring herbicide resistance.

As used herein, the term "confer" refers to providing a characteristic or trait, such as herbicide tolerance or resistance and/or other desirable traits to a plant.

Disclosed here is a method for rendering crop plants (corn, rice, maize, wheat, barley, soybean, rape/canola, cotton etc.) tolerant to herbicides that act by inhibiting the enzyme hydroxyphenylpyruvate dioxygenase (HPPD), or other herbicides such as Benzothiadiazinones, Sulfonylureas, and other classes of herbicides including, for example, Imidazolinones, Triazolopyrimidines, Pyrimidinylthiobenzoates, Triazolinones, Auxins, Acetyl-coenzyme A Carboxylase (ACCase) inhibitors, Photosystem II (PSII) inhibitors, Protoporphyrinogen Oxidase (PPO) inhibitors, Phytoene Desaturase (PDS) inhibitors, Dinitroanalines, and Acetamides, as well as herbicides with unknown modes of action such as Difenzoquat and Clomazone.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Cytochrome P450 Sequences

Cytochrome P450 sequences are provided that confer herbicide tolerance or resistance. Such sequences include the amino acid sequences set forth in SEQ ID NOS:1, 3, and 5, and variants thereof. Also provided are polynucleotide sequences encoding such amino acid sequences, including SEQ ID NOS:2, 4, and 6.

According to the method of the present disclosure crop plants are transformed with a gene encoding a cytochrome P450 enzyme (CYP enzymes) capable of oxidising certain HPPD-inhibitors and also, optionally, other types of herbicides. The gene cassette comprises promoter and terminator regions and, optionally, other elements (such as introns, transcriptional enhancers, translational enhancers etc.) so as to provide for expression of an effective amount of the P450 enzyme in the crop plant. Optionally the structural gene encoding the P450 enzyme is codon optimised to remove features inimical to expression and codon usage is optimised for expression in the particular crop (see, for example, U.S. Pat. No. 6,051,760; EP 0359472; EP 80385962; EP 0431829; and Perlak et al. (1991) *PNAS USA* 88:3324-3328; all of which are herein incorporated by reference). In certain embodiments the P450 enzyme is selected as one capable of oxidising 'other' herbicides that include nicosulfuron and/or bentazon, and/or as capable of oxidising the HPPD-inhibitor herbicide mesotrione and/or sulcotrione. In another embodiment, the P450 enzyme is selected as one capable of oxidising HPPD-inhibitors that include, but are not limited to, Mesotrione, SYN449280, Isoxaflutole, Tembotrione, Topramezone, Pyrasulfatole, Sulcotrione, Pyrazolynate, Pyrazoxyfen, Isoxachlortole, Benzofenap, and Benzobicyclon.

Examples of optimized genes encoding a cytochrome P450 enzyme for use in the present invention include corn nsf1 (SEQ ID NO: 1), corn CYP72A1 (SEQ ID NO:3), and rice CYP81A6 (SEQ ID NO:5). Other polynucleotides of interest that encode a cytochrome P450 enzyme for use in the present invention include, but are not limited to, polynucleotides encoding the amino acid sequence for corn nsf1 (SEQ ID NO:2); corn CYP72A1 (SEQ ID NO:4), and rice CYP81A6 (SEQ ID NO:6).

Additional polynucleotide sequences encoding a cytochrome P450 enzyme for use in the present invention may be identified using methods well known in the art based on their ability to confer resistance or tolerance to an herbicide of interest. For example, candidate P450 genes are transformed into and expressed in suitable yeast strains and selected on the basis of their ability to oxidise test herbicides in vitro (cf Siminszky et al (1999) *PNAS* (USA) 96:1750-1755). Suitable yeast strains include such as WAT11 or WAT21 which also comprise a suitable plant cytochrome P450 competent reductase (e.g. as described by Denis Pompon and Phillipe Urban). Following induction for a suitable period (for example, depending on the inducible promoter used in the transformation vector, with galactose) cells are grown up, harvested, broken, the microsome fraction prepared by the usual means and assayed with NADPH for the ability to oxidise 14C-labelled mesotrione. Optionally, assays are carried out using whole cells in culture. The oxidised products with 4 and 5 hydroxy modifications of the cyclohexanedione ring are easily detected and separated from unmodified parent by, for example, RP HPLC or TLC (cf Hawkes et al. 2001, BCPC conference Weeds, p563).

Alternatively, candidate P450 enzymes are expressed in tobacco, *Arabidopsis*, corn or other easily transformed, herbicide sensitive plant and the resultant transformant plants assessed for their tolerance to HPPD inhibitor(s) (as described in Didierjean et al. (2002) *Plant Physiol.* 130:179-189) or other herbicides of interest. Optionally the plants, or tissue samples taken from plants, are treated with herbicide and assayed in order to assess the rate of metabolic conversion of parent herbicide to oxidised metabolic degradation products. For example, radiolabeled mesotrione is used along with analytical methods described in Hawkes et al 2001, BCPC conference Weeds, p563; Alferness and Wiebe (2002) *J. Agric. Food Chem.*, 50:3926-3934 and/or Gledhill et al (2004) Xenobiotica 31, 733-747. Suitable gene constructs for expressing the cytochrome P450 encoding sequence in crop plants comprise a plant suitable promoter and 5' leader sequence upstream (for example the CMV 35 S promoter or an actin promoter region) and a suitable terminator sequence (to ensure polyadenylation) downstream (for example the nos gene 3' sequence) of the cytochrome P450 coding sequence. Optionally, constructs may comprise additional sequences such as translational and transcriptional enhancers and/or the DNA sequence is modified for optimal expression in the host plant.

As used herein, a significant rate of oxidation is defined as a catalytic rate sufficient to provide a clear (greater than about 2x) increase in tolerance to a given substrate herbicide in a transgenic plant, where the transgenic plant expresses a given P450 enzyme at up to 0.2% of the total cellular protein relative to a similarly treated non-transgenic control plant.

In one embodiment of the present disclosure, genes encoding suitable P450 enzymes are selected from maize or rice cDNA libraries prepared by standard methods (e.g. using the lambda-ZAPII vector kit from Stratagene) from 3-7 day old seedlings of maize or rice plants. Optionally, suitable candidate P450-encoding sequences are selected from amongst those P450s induced within approximately 24 h treatment with 1-50 ppm mesotrione or other HPPD inhibitor, or with nicosulfuron. In addition, suitable candidate P450 encoding sequences are selected from amongst those P450s induced in maize tissues within 24 h of treatment with safening levels of cyprosulfamide, isoxadifen and/or CGA24678; or alternatively in other cereals following treatment with cloquintacet and/or mefenpyr. This can be readily accomplished by measuring (relative) transcript levels via northern blot analysis, differential display analysis, and/or with a RNA Chip, containing probes for all, or a majority of the P450 genes of the plant species of interest. Alternatively, a library is screened by PCR and, for example, the incorporation of radio labelled nucleotide used to detect clones comprising the characteristic heme-binding region of cytochrome P450s. For example degenerate 5' primers for the heme motif region (Ohbayashi et al 1993) can be used along with 3' primers designed for the poly A tail (cf. Persans et al (2001) *Plant physiol.*, 125:1126). The, so-produced, labelled PCR products are used to rescreen the library to recover full-length cDNAs which are then sequenced. Candidate P450 genes are obtained for example by the above method or by other methods known in the art (cf U.S. Pat. No. 6,380,465 and U.S. Pat. No. 6,121,512 and all references cited within; cf Persans et al (2001) *Plant physiol.*, 125:1126) and are then selected via a process of expressing them and assayed for their ability to oxidise (or provide resistance) to especially mesotrione or other HPPD inhibitor(s) or nicosulfuron in a suitable test system.

An alternative method for selecting suitable P450 enzymes is through genetic mapping of P450 genes involved in resistance to the herbicide of interest. If lines exist with tolerance and lines with resistance to the herbicide, based on differential P450 responses, this is possible. For an example of fine structure QTL mapping and sequencing of candidate CYP genes (readily recognisable through sequence homologies and by their characteristic heme motif; see Bortiri et al. (2006) *Current Opinion in Plant Biology* 9:164-171). For example, certain lines and hybrids of sweetcorn (e.g. Merit) are susceptible to mesotrione and through conventional crossing studies with tolerant varieties and the use of markers it is possible to map QTLs associated with this susceptibility. We have previously shown that mesotrione levels in treated corn plants decrease over time, due to a P450 based degradation mechanism. Merit plants appear defective in this degradation step. Thus, the QTLs associated with the differential response are expected to contain a P450 gene, or genes, that degrade mesotrione. If genomic sequences exist for the mapping interval, candidate CYP gene can be identified. Alternatively, BACS (Bacterial Artificial Chromosome clones) encompassing the QTL are sequenced and candidate CYP genes identified. By comparing the sequences of the P450 alleles in the tolerant and sensitive varieties, the candidate CYP genes be identified (and particularly easily if, for example, there is an obvious gene defect and/or lack of expression in sensitive varieties).

For example, relevant to the current invention, it is known that a small number of corn lines are sensitive to mesotrione, and a small number are sensitive to nicosulfuron. These 2 groups overlap partially (see HortScience (2005) 40:1801-1805 and the list in Table 1). Table 1 is based on screening of corn lines with mesotrione and nicosulfuron (by Syngenta, Toulouse, F R). Only the lines with the highest tolerance and highest sensitivity are shown, from screening ~400 lines.

TABLE 1

A general correlation exists between tolerance to mesotrione or nicosulfuron, and sensitivity to mesotrione and nicosulfuron*.

| Line Code | Callisto® treatment** | Milagro® treatment*** |
|---|---|---|
| BX20009 | 1 | 3 |
| IAFX239 | 1 | 4 |
| FX7179 | 1 | 3 |
| PC7505 | 1 | 1 |
| FB7768 | 1 | 5 |
| IC3008HG | 1 | 1 |
| PJ7501 | 1.5 | 2 |
| FB7456 | 2 | 2 |
| FB7556 | 2 | 4 |
| IC4612 | 2 | 4 |
| IG5226 | 2 | 3 |
| HX904 | 2 | 3 |
| ICFX234 | 2 | 4 |
| ICFX235 | 2 | 4 |
| FX8236 | 2 | 2 |
| FX7422 | 2 | 2 |
| FX7423 | 2 | 4 |
| FX7425 | 2 | 2 |
| FX7521 | 2 | 3 |
| FX7527 | 2 | 4 |
| ICPC407 | 2 | 1 |
| PJ7502 | 2 | 5 |
| PJ8619 | 2 | 5 |
| FA3112 | 2 | 4 |
| CO5041 | 2 | 1 |
| ID5401 | 2 | 5 |
| IC3008 | 2 | 1 |
| IC3008GF | 2 | 2 |
| ID3461 | 2 | 3 |
| FX7093 | 2 | 3 |
| XDOP735 | 2 | 1 |
| CC8962 | 2 | 1 |
| OX7010 | 2 | 2 |
| XXFO001 | 2 | 3 |
| CH5001 | 2 | 3 |
| BX214 | 7 | 5 |
| EH019HL | 7 | 1 |
| FAAX165 | 7 | 3 |
| NW0351 | 7 | 9 |
| NW1395 | 7 | 6 |
| FPNW462-2-1 | 7 | 8 |
| FPNW561 | 7 | |
| FPWR868 | 7 | 7 |
| FSNU505HG | 7 | 2 |
| FSNU929HG | 7 | 2 |
| GUID354 | 7 | 6 |
| HX911 | 7 | 5 |
| JP7084 | 7 | 7 |
| MC8629 | 7 | 6 |
| ICPJ635 | 7 | 6 |
| FA7278 | 7 | 3 |
| N60028 | 7 | 4 |
| CH6150 | 7 | 6 |
| UM12 | 7 | 6 |
| XDFF207 | 7 | 3 |
| XFNO355 | 7 | 4 |
| XICC310 | 7 | 4 |
| DH6901 | 7 | 6 |
| XPCC002 | 7 | 3 |
| XPEO001 | 7 | 4 |
| NU1936 | 7.5 | 5 |
| CX329 | 8 | 7 |
| HI4006 | 8 | 4 |

*Scale used for scoring: 1 to 9 scale, where 1 = most resistant lines and 9 = most susceptible lines. Unshaded boxes are genotypes most resistant to mesotrione (Callisto ®). Shaded boxes are genotypes most susceptible to mesotrione (Callisto ®).
**Callisto ® (Mesotrione) treatment: concentration equivalent to 60 g of active matter/ha, spray at stage V2, score 10 days after spray.
***Milagro ® (nicosufuron) treatment: concentration equivalent to 24 g of active matter/ha, spray at stage V2, score 10 days after spray.

Genetic analysis indicates that the genes that confer the tolerance/susceptibility to mesotrione and nicosulfuron are closely linked in the corn genome. M. Williams et al. (2006, Corn Genetics Conference, Asiloma), used a map based cloning approach to clone the P450 gene that conditions the nicosulfuron response of corn plant, the nsf1 gene, located in bin 5.01. One mesotrione tolerance QTL in corn lines with susceptibility to mesotrione and sulcotrione (a close homolog of mesotrione) has been mapped, to corn genome position bin 5.01. We sequenced this gene from B73 BAC b0159B4, and deduced the amino acid sequence (SEQ ID NO:1). A second and third P450 gene are located on this nsf1 containing BAC (genes 160842 and 136090) SEQ ID NO:7 and SEQ ID NO:8 are the deduced amino acid sequences from these 2 P450 genes.

Thus, all 3 P450 genes above are candidate P450 gene capable of degrading mesotrione. In addition, all of the genes/P450 enzymes listed in the Listing of Sequences (FIG. 2) are candidate genes for use in the present invention.

Suitable P450 genes are thus selected from the list comprising the above candidate cytochrome P450 genes obtainable by the above described methods and including those from maize and from rice and also other species, including for example *Catharanthus roseus* (SEQ ID NO:9; see also the Listing of Sequences, FIG. 2).

Once one P450 gene capable of degrading these herbicides is identified, those skilled in the art may also find further gene candidates based on genome synteny and sequence similarity. In one embodiment, additional gene candidates can be obtained by hybridization or PCR using sequences based on the cytochrome P450 nucleotide sequences noted above.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See, for example, Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

By "hybridizing to" or "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

The present invention also relates to the use of cytochrome P450 or variants thereof that confer resistance or tolerance to HPPD inhibitors, benzothiadiazinones, sulfonylureas, and other classes of herbicides. "Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode cytochrome P450 enzymes described above for use in the present invention. Naturally occurring allelic variants can be identified with the use of well-known molecular biology techniques, as, for example, with polymerase chain reaction (PCR) and hybridization techniques as outlined above. Variant polynucleotides also include synthetically derived polynucleotides, such as those generated, for example, by using site-directed mutagenesis but which still encode a cytochrome P450 enzyme conferring herbicide resistance or tolerance. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide.

Variants of a particular polynucleotide encoding a cytochrome P450 that confers herbicide resistance or tolerance are encompassed by the present invention and can be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and algorithms described below. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Methods of alignment of sequences for comparison are well known in the art and can be accomplished using mathematical algorithms such as the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; and the algorithm of Karlin and Altschul (1990) *Proc. Natl. Acad. Sci. USA* 872264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Essentially similar methods of gene mutagenesis and selection based on improved tolerance or resistance as described elsewhere herein can also be used to generate and select improved variants of the cytochrome P450 genes of the current invention.

Gene Stacking

In certain embodiments the polynucleotides encoding a cytochrome P450 or variant thereof that confers herbicide resistance or tolerance can be stacked with any combination of polynucleotide sequences of interest in order to create plants with a desired trait. A trait, as used herein, refers to the phenotype derived from a particular sequence or groups of sequences. For example, the polynucleotides encoding a cytochrome P450 or variant thereof that confers herbicide resistance or tolerance may be stacked with any other polynucleotides encoding polypeptides that confer a desirable trait, including but not limited to resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

Exemplary polynucleotides that may be stacked with polynucleotides encoding an herbicide resistant or tolerant cytochrome P450 or variant thereof include polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) *Science,* 304:1151-1154; and in U.S. Patent App. Pub. Nos. 20070004912, 20050246798, and 20050060767)); glufosinate resistance (e.g., phosphinothricin acetyl transferase genes PAT and BAR, described in U.S. Pat. Nos. 5,561,236 and 5,276,268); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference.

Thus, in one embodiment, the polynucleotides encoding a cytochrome P450 or variant thereof that confers herbicide resistance or tolerance are stacked with one or more polynucleotides encoding polypeptides that confer resistance or tolerance to an herbicide. In one embodiment, the desirable trait is resistance or tolerance to an HPPD inhibitor. In another embodiment, the desirable trait is resistance or tolerance to glyphosate. In another embodiment, the desirable trait is resistance or tolerance to glufosinate.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

In one embodiment the crop plant is transformed not only with a gene to express said P450 enzyme but is also transformed with a gene to express an heterologous HPPD enzyme. The P450 gene and the HPPD gene may be introduced into separate events, and these events or their progeny crossed so as to combine the genes in a single plant. Alternatively, both the P450 and HPPD genes are combined within a single DNA molecule which is transformed into the crop plant. In a further embodiment the HPPD gene is derived from a monocot plant, a cereal plant or, more preferably a wheat, *Avena* or corn plant and is, for example, as disclosed in PCT application WO 02/46387. Optionally, the HPPD enzyme may be targeted to cellular locations, to enhance expression/ accumulation levels, or to enhance activity levels. For instance, the HPPD may be plastid-targeted through fusion with a suitable transit peptide. Suitable HPPD genes, constructs, promoter regions, 5' leader sequences, terminators etc for expressing HPPD in crop plants are, for example, also described in WO 0246387, WO 0032757, and WO 9904021. Optionally, the HPPD gene may be directly transformed into the plastome of the chloroplast of the target plant, for high level enzyme accumulation.

In a further embodiment the HPPD gene sequence encodes the *Avena* HPPD enzyme sequence which is SEQ ID NO:10 here (SEQ ID NO:4 in WO 0246387) with the following slight sequence modifications within the N terminal part of the protein. The sequence motif AATAAATASIPS within SEQ ID NO: 10 is shortened to read AATAATASIPS (SEQ ID NO: 11) or altered to read AATAATTASIPS (SEQ ID NO:12) or altered to read AADAAATASIPS (SEQ ID NO:13) or any combination of these 3 changes is made. The resultant enzymes are described as 'modified-Avena HPPD'. In one embodiment, the crop plant is transformed with a gene encoding a cytochrome P450 enzyme selected from the group consisting of nsf1 (SEQ ID NO:1), corn CYP72A1 (SEQ ID NO:3), and rice CYP81A6 gene (SEQ ID NO: 5), in combination with a gene sequence encoding a modified-Avena HPPD.

In a further embodiment, the *Avena* gene, for example, or another plant-derived HPPD sequence is modified to enhance the tolerance to one or more HPPD inhibitors (see, e.g., U.S. Patent App. Pub. No. 20080076178, incorporated herein by reference in its entirety). The resultant enzymes are described as 'modified-HPPD'. Standard methodologies known in the art can be used to introduce changes in the HPPD enzyme gene, that lead to enhanced tolerance of the encoded enzyme to HPPD enzyme inhibitors. These methodologies include gene shuffling, directed mutations, random mutations, and Gene Site Saturated Mutagenesis (GSSM). Putative HPPD gene mutants can be screened in biological systems for activity in the presence of inhibitors, present at concentrations that inhibit wild type enzymes.

Suitable resistant and functional HPPD gene mutants can be selected by many methods well known in the art. For example candidate HPPD encoding sequences produced by mutagenesis are expressed in yeast, in a bacterial host strain, in an alga or in a higher plant such as tobacco or *Arabidopsis* and the relative levels of inherent tolerance of the HPPD encoding sequences screened according to the observed levels of resistance or tolerance or, alternatively, a visible indicator phenotype of the transformed strain or plant in the presence of different concentrations of the selected HPPD inhibitors. Dose responses and relative shifts in dose responses associated with these indicator phenotypes (formation of brown colour, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD. After identification of suitable resistant and functional gene mutants, the encoded enzymes can be further analyzed by kinetic analysis, for instance for enzyme activity, and inhibitor binding characteristics.

Many combinations of host organism, indicator phenotype and control HPPD would achieve a similar scope of selection and these are contemplated within the scope of the current invention. For example, in a relatively rapid assay system based upon transformation of a bacterium such as *E. coli*, each HPPD encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different HPPD sequences. Such strains expressing polynucleotides comprising alternative candidate HPPD sequences may be plated out on different concentrations of the selected herbicides in, optionally, a tyrosine supplemented medium and the relative levels of inherent tolerance of the expressed HPPD enzymes estimated on the basis of the extent and MIC for inhibition of the formation of the brown, ochronotic pigment. In variations of the method the cells may be permeabilized or, particularly in the case of yeast, be strains having disabled pumps in order to minimise the effects of differential uptake and export of HPPD inhibitors into and out of the cell. In one variation, bacterial cells are grown almost to stationary phase in a liquid medium, exposed to selected herbicides for a short period of one hour or less, resuspended in a similar volume of fresh medium and the rate of development of pigment monitored. In another variation, candidate HPPD expressing sequences are transferred to a shuttle vector and, similar to the previous variation, are each expressed at a comparable level, but in this case in a suitable *Pseudomonas* species such as *Pseudomonas fluorescens* capable of being transformed and of growing on tyrosine as sole carbon source. Preferably the endogenous HPPD gene of the host *Pseudomonas* line is knocked out, for example, by recombinational insertion of an antibiotic marker gene. *Pseudomonas* lines each transformed to express an alternative resistant HPPD enzyme are each grown on different concentrations of selected HPPD inhibitors and the inherent resistance of the expressed HPPD sequence in respect of each HPPD inhibitor estimated upon the basis of the concentration necessary to prevent growth on a medium containing tyrosine as sole carbon source. In a final selection step a short list of candidate polynucleotides may be transformed into plant material, which material is regenerated into morphologically normal fertile plants and which plants are then measured for differential tolerance to selected HPPD-inhibitor herbicides.

Plant Expression Cassettes

The compositions of the invention may additionally contain nucleic acid sequences for transformation and expression in a plant of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., an herbicide resistant or tolerant cytochrome P450 polynucleotide, alone or in combination with one or more additional nucleic acid molecules encoding polypeptides that confer desirable traits) which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing a polynucleotide of interest, i.e., a polynucleotide encoding a cytochrome P450 or variant thereof that confers herbicide resistance or tolerance, alone or in combination with one or more additional nucleic acid molecules encoding polypeptides that confer desirable traits. The expression cassette will include in the 5'-3' direction of transcription, a transcriptional and translational initiation region (i.e., a promoter) and a polynucleotide of. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) *Plant J* 34:383-92 and Chen et al. (2003) *Plant J* 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence. The promoters that are used for expression of the transgene(s) can be a strong plant promoter, a viral promoter, or a chimeric promoters composed of elements such as: TATA box from any gene (or synthetic, based on analysis of plant gene TATA boxes), optionally fused to the region 5' to the TATA box of plant promoters (which direct tissue and temporally appropriate gene expression), optionally fused to 1 or more enhancers (such as the 35S enhancer, FMV enhancer, CMP enhancer).

Exemplary constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Appropriate plant or chimeric promoters are useful for applications such as expression of transgenes in certain tissues, while minimizing expression in other tissues, such as seeds, or reproductive tissues. In some embodiments expression of the cytochrome P450 gene of the current invention may optionally be localised to seed or fruit tissues in order to further oxidise away any residue of parent herbicide reaching these tissues. Exemplary cell type- or tissue-preferential promoters drive expression preferentially in the target tissue, but may also lead to some expression in other cell types or tissues as well. Methods for identifying and characterizing promoter regions in plant genomic DNA include, for example, those described in the following references: Jordano, et al., *Plant Cell,* 1:855-866 (1989); Bustos, et al., *Plant Cell,* 1:839-854 (1989); Green, et al., *EMBO J.* 7, 40354044 (1988); Meier, et al., *Plant Cell,* 3, 309-316 (1991); and Zhang, et al., *Plant Physiology* 110: 1069-1079 (1996).

In other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1:1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711 (1987); Skuzeski et al *Plant Molec. Biol.* 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Plants

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Plants useful in the present invention include plants that are transgenic for at least a polynucleotide encoding a cytochrome P450 or variant thereof that confers herbicide resistance or tolerance, alone or in combination with one or more additional nucleic acid molecules encoding polypeptides that confer desirable traits. The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

Plants according to the present invention include any plant that is cultivated for the purpose of producing plant material that is sought after by man or animal for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass and the like. It is recognized that mixtures of plants may be used.

In addition, the term "crops" is to be understood as including crops that have been rendered tolerant to herbicides or classes of herbicides (such as, for example, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. Examples of crops that have been rendered tolerant to herbicides or classes of herbicides by genetic engineering methods include glyphosate- and glufosinate-resistant crop varieties commercially available under the trade names RoundupReady® and LibertyLink®. The method according to the present invention is especially suitable for the protection of soybean crops which have also been rendered tolerant to glyphosate and/or glufosinate and where HPPD herbicides are used in a weed control programme along with other such herbicides (glufosinate and/or glyphosate) for weed control.

It is further contemplated that the constructs of the invention may be introduced into plant varieties having improved properties suitable or optimal for a particular downstream use. For example, naturally-occurring genetic variability results in plants with resistance or tolerance to HPPD inhibitors or other herbicides, and such plants are also useful in the methods of the invention. The method according to the present invention can be further optimized by crossing the transgenes that provide a level of tolerance, with soybean cultivars that exhibit an enhanced level of tolerance to HPPD inhibitors that is found in a small percentage of soybean lines.

Plant Transformation

Once an herbicide resistant or tolerant cytochrome P450 polynucleotide, alone or in combination with one or more additional nucleic acid molecules encoding polypeptides that confer desirable traits, has been cloned into an expression system, it is transformed into a plant cell. The receptor and target expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra Gene 19: 259-268 (1982); Bevan et al., Nature 304:184-187 (1983)), the pat and bar genes, which confer resistance to the herbicide glufosinate (also called phosphinothricin; see White et al., Nucl. Acids Res 18: 1062 (1990), Spencer et al. Theor. Appl. Genet. 79: 625-631 (1990) and U.S. Pat. Nos. 5,561,236 and 5,276,268), the hph gene, which confers resistance to the antibiotic hygromycin (Blochinger & Diggelmann, Mol. Cell. Biol. 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), the glyphosate N-acetyltransferase (GAT) gene, which also confers resistance to glyphosate (Castle et al. (2004) Science, 304:1151-1154; U.S. Patent App. Pub. Nos. 20070004912, 20050246798, and 20050060767); and the mannose-6-phosphate isomerase gene, which provides the ability to metabolize mannose (U.S. Pat. Nos. 5,767,378 and 5,994,629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

Many vectors are available for transformation using Agrobacterium tumefaciens. These typically carry at least one T-DNA border sequence and include vectors such as pBIN19 (Bevan, Nucl. Acids Res. (1984)). For the construction of vectors useful in Agrobacterium transformation, see, for example, US Patent Application Publication No. 2006/0260011, herein incorporated by reference.

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell* 2: 603-618 (1990)) and Fromm et al. (*Biotechnology* 8: 833-839 (1990)) have published techniques for transformation of A188-derived maize line using particle bombardment. Furthermore, WO 93/07278 and Koziel et al. (*Biotechnology* 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. *Plant Cell Rep* 7: 379-384 (1988); Shimamoto et al. *Nature* 338: 274-277 (1989); Datta et al. *Biotechnology* 8:736-740 (1990)). Both types are also routinely transformable using particle bombardment (Christou et al. *Biotechnology* 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (*Biotechnology* 10: 667-674 (1992)) using particle bombardment into cells of type C long-term regenerable callus, and also by Vasil et al. (*Biotechnology* 11:1553-1558 (1993)) and Weeks et al. (*Plant Physiol.* 102:1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, *Physiologia Plantarum* 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., *Plant Cell Reports* 19: 798-803 (2000), incorporated herein by reference.

For example, rice (*Oryza sativa*) can be used for generating transgenic plants. Various rice cultivars can be used (Hiei et al., 1994, *Plant Journal* 6:271-282; Dong et al., 1996, *Molecular Breeding* 2:267-276; Hiei et al., 1997, *Plant Molecular Biology*, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (Agrobacterium) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., *In Vitro Cell. Dev. Biol.-Plant* 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of interest in the present invention can be any of a wide variety of plant species, including those of monocots and dicots; however, the plants used in the method of the invention are preferably selected from the list of agronomically important target crops set forth elsewhere herein. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) *PNAS* 90, 913-917). Bombarded seedlings are incubated on T medium for two days after which leaves are excised and placed abaxial side up in bright light (350-500 umol photons/m$^2$/s) on plates of RMOP medium (Svab, Z., Hajdukiewicz, P. and Maliga, P. (1990) *PNAS* 87, 8526-8530) containing 500 ug/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) *Plant Mol Biol Reporter* 5, 346349) is separated on 1% Tris-borate (TBE) agarose gels, transferred to nylon membranes (Amersham) and probed with .sup.32P-labeled random primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride, K. E. et al (1994) *PNAS* 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

Many suitable methods for transformation using suitable selection markers such as kanamycin, binary vectors such as from *Agrobacterium* and plant regeneration as, for example, from tobacco leaf discs are well known in the art. Optionally, a control population of plants are likewise transformed with a polynucleotide expressing the control HPPD. Alternatively, an untransformed dicot plant such as *Arabidopsis* or Tobacco can be used as a control since this, in any case, expresses its own endogenous HPPD.

Herbicide Resistance

The present invention provides transgenic plants, plant cells, tissues, and seeds that have been transformed with a nucleic acid molecule encoding a cytochrome P450 or variant thereof that confers resistance or tolerance to herbicides, alone or in combination with one or more additional nucleic acid molecules encoding polypeptides that confer desirable traits.

In one embodiment, the transgenic plants of the invention exhibit resistance or tolerance to application of herbicide in an amount of from about 5 to about 2,000 grams per hectare (g/ha), including, for example, about 5 g/ha, about 10 g/ha, about 15 g/ha, about 20 g/ha, about 25 g/ha, about 30 g/ha, about 35 g/ha, about 40 g/ha, about 45 g/ha, about 50 g/ha, about 55 g/ha, about 60 g/ha, about 65 g/ha, about 70 g/ha, about 75 g/ha, about 80 g/ha, about 85 g/ha, about 90 g/ha, about 95 g/ha, about 100 g/ha, about 110 g/ha, about 120 g/ha, about 130 g/ha, about 140 g/ha, about 150 g/ha, about 160 g/ha, about 170 g/ha, about 180 g/ha, about 190 g/ha, about 200 g/ha, about 210 g/ha, about 220 g/ha, about 230 g/ha, about 240 g/ha, about 250 g/ha, about 260 g/ha, about 270 g/ha, about 280 g/ha, about 290 g/ha, about 300 g/ha, about 310 g/ha, about 320 g/ha, about 330 g/ha, about 340 g/ha, about 350 g/ha, about 360 g/ha, about 370 g/ha, about 380 g/ha, about 390 g/ha, about 400 g/ha, about 410 g/ha, about 420 g/ha, about 430 g/ha, about 440 g/ha, about 450 g/ha, about 460 g/ha, about 470 g/ha, about 480 g/ha, about 490 g/ha, about 500 g/ha, about 510 g/ha, about 520 g/ha, about 530 g/ha, about 540 g/ha, about 550 g/ha, about 560 g/ha, about 570 g/ha, about 580 g/ha, about 590 g/ha, about 600 g/ha, about 610 g/ha, about 620 g/ha, about 630 g/ha, about 640 g/ha, about 650 g/ha, about 660 g/ha, about 670 g/ha, about 680 g/ha, about 690 g/ha, about 700 g/ha, about 710 g/ha, about 720 g/ha, about 730 g/ha, about 740 g/ha, about 750 g/ha, about 760 g/ha, about 770 g/ha, about 780 g/ha, about 790 g/ha, about 800 g/ha, about 810 g/ha, about 820 g/ha, about 830 g/ha, about 840 g/ha, about 850 g/ha, about 860 g/ha, about 870 g/ha, about 880 g/ha, about 890 g/ha, about 900 g/ha, about 910 g/ha, about 920 g/ha, about 930 g/ha, about 940 g/ha, about 950 g/ha, about 960 g/ha, about 970 g/ha, about 980 g/ha, about 990 g/ha, about 1,000 g/ha, about 1,010 g/ha, about 1,020 g/ha, about 1,030 g/ha, about 1,040 g/ha, about 1,050 g/ha, about 1,060 g/ha, about 1,070 g/ha, about 1,080 g/ha, about 1,090 g/ha, about 1,100 g/ha, about 1,110 g/ha, about 1,120 g/ha, about 1,130 g/ha, about 1,140 g/ha, about 1,150 g/ha, about 1,160 g/ha, about 1,170 g/ha, about 1,180 g/ha, about 1,190 g/ha, about 1,200 g/ha, about 1,210 g/ha, about 1,220 g/ha, about 1,230 g/ha, about 1,240 g/ha, about 1,250 g/ha, about 1,260 g/ha, about 1,270 g/ha, about 1,280 g/ha, about 1,290 g/ha, about 1,300 g/ha, about 1,310 g/ha, about 1,320 g/ha, about 1,330 g/ha, about 1,340 g/ha, about 1,350 g/ha, about 360 g/ha, about 1,370 g/ha, about 1,380 g/ha, about 1,390 g/ha, about 1,400 g/ha, about 1,410 g/ha, about 1,420 g/ha, about 1,430 g/ha, about 1,440 g/ha, about 1,450 g/ha, about 1,460 g/ha, about 1,470 g/ha, about 1,480 g/ha, about 1,490 g/ha, about 1,500 g/ha, about 1,510 g/ha, about 1,520 g/ha, about 1,530 g/ha, about 1,540 g/ha, about 1,550 g/ha, about 1,560 g/ha, about 1,570 g/ha, about 1,580 g/ha, about 1,590 g/ha, about 1,600 g/ha, about 1,610 g/ha, about 1,620 g/ha, about 1,630 g/ha, about 1,640 g/ha, about 1,650 g/ha, about 1,660 g/ha, about 1,670 g/ha, about 1,680 g/ha, about 1,690 g/ha, about 1,700 g/ha, about 1,710 g/ha, about 1,720 g/ha, about 1,730 g/ha, about 1,740 g/ha, about 1,750 g/ha, about 1,760 g/ha, about 1,770 g/ha, about 1,780 g/ha, about 1,790 g/ha, about 1,800 g/ha, about 1,810 g/ha, about 1,820 g/ha, about 1,830 g/ha, about 1,840 g/ha, about 1,850 g/ha, about 1,860 g/ha, about 1,870 g/ha, about 1,880 g/ha, about 1,890 g/ha, about 1,900 g/ha, about 1,910 g/ha, about 1,920 g/ha, about 1,930 g/ha, about 1,940 g/ha, about 1,950 g/ha, about 1,960 g/ha, about 1,970 g/ha, about 1,980 g/ha, about 1,990 g/ha, or about 2,000.

The average and distribution of herbicide tolerance or resistance levels of a range of primary plant transformation events are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent inhibitor-tolerance (increased Ki value) of the expressed HPPD.

The methods of the present invention are especially useful to protect soya crops from the herbicidal injury of HPPD inhibitor herbicides of the classes of HPPD chemistry selected from the group consisting of the compounds of formula Ia

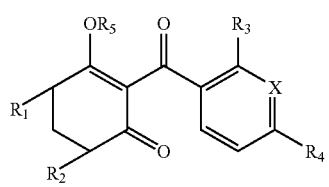
(Ia)

wherein $R_1$ and $R_2$ are hydrogen or together an ethylene bridge;

$R_3$ is $C_1$-$C_4$alkyl, halogen, nitro, $C_1$-$C_4$alkoxy-$C_1$-$C_4$alkyl, $C_1$-$C_4$alkoxy-$C_1$-$C_4$alkoxy-$C_1$-$C_4$alkyl or $R_3$ is a group

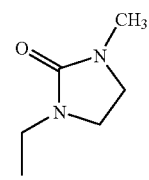

$R_4$ is $C_1$-$C_4$alkylsulfonyl or $C_1$-$C_4$haloalkyl;

$R_5$ is hydrogen or phenylthio; X is methine, nitrogen or C—$R_6$, wherein $R_6$ is $C_1$-$C_4$haloalkoxy-$C_1$-$C_4$alkyl or a group

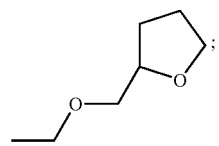

the compounds of formula Ib

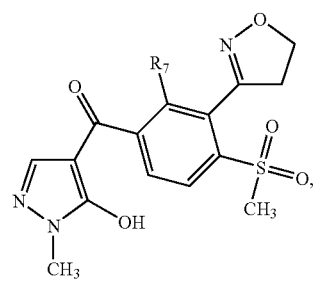
(Ib)

wherein $R_7$ is methyl or chlorine; the compounds of formula Ic

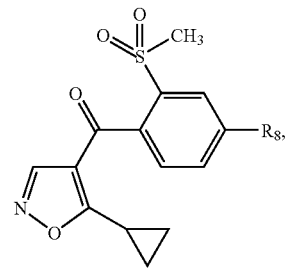
(Ic)

wherein $R_8$ is halogen or $C_1$-$C_4$haloalkyl; the compound of formula Id

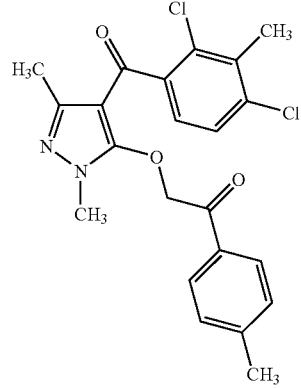

the compound of formula Ie

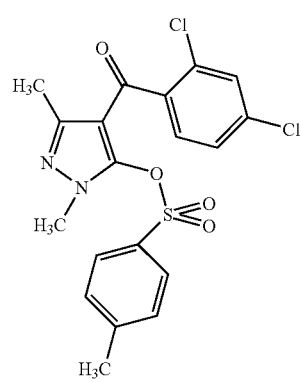

the compound of formula If

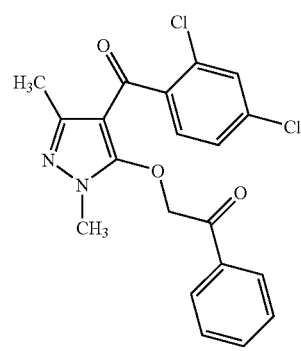

the compound of formula Ig

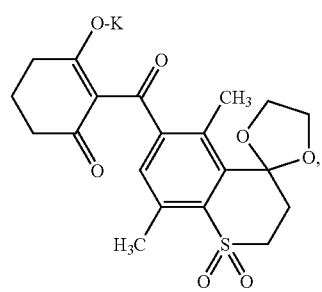

and the free acid thereof, the compound of formula Ih

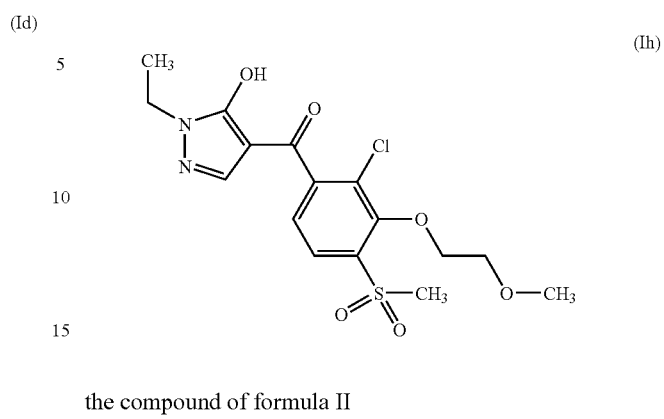

the compound of formula Ii

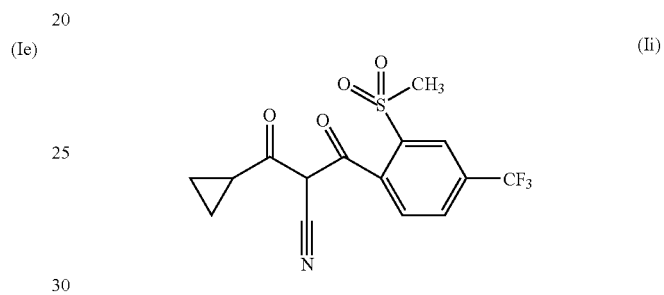

the compound of formula Ij

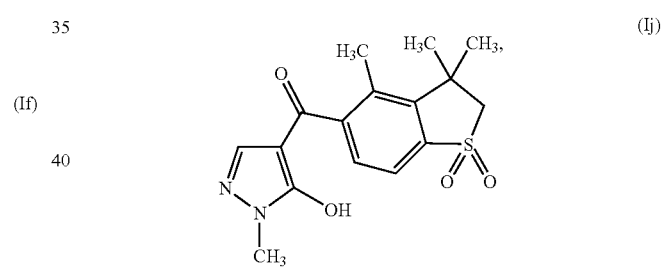

and the compound of formula Ik

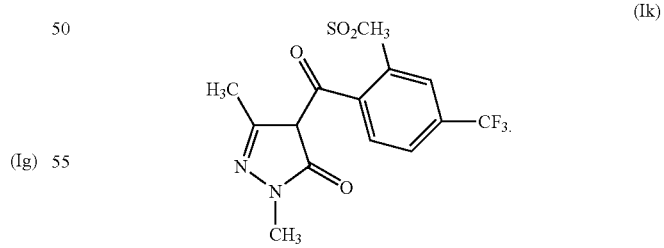

The alkyl groups appearing in the substituent definitions may be straight-chain or branched and are, for example, methyl, ethyl, n-propyl, isopropyl, n-butyl, sec-butyl, isobutyl or tert-butyl. Halogen is generally fluorine, chlorine, bromine or iodine, preferably fluorine or chlorine. The same is true of halogen in conjunction with other meanings, such as haloalkyl.

Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl; preferably trichloromethyl, difluorochloromethyl, difluoromethyl, trifluoromethyl or dichlorofluoromethyl.

Alkoxyalkoxy groups preferably have a chain length of from 1 to 8 carbon atoms. Examples of alkoxyalkoxy are: methoxymethoxy, methoxyethoxy, methoxypropoxy, ethoxymethoxy, ethoxyethoxy, propoxymethoxy and butoxybutoxy. Alkoxyalkyl groups have a chain length of preferably from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxy-alkoxy-alkyl groups preferably have a chain length of from 1 to 8 carbon atoms. Examples of alkoxyalkoxy-alkyl are: methoxymethoxymethyl, methoxyethoxymethyl, ethoxymethoxymethyl and methoxyethoxyethyl.

The compounds of formula Ia to Ik are known or can be prepared according to known methods. Compounds of formula Ia and their preparation are known from WO/0015615, WO/0015615, WO 02/085118, WO 00/021924, U.S. Pat. No. 5,006,158 (and U.S. Pat. No. 4,780,127. Compounds of formula Ib are described in WO 98/31681, and mixtures of those compounds with herbicides are known from WO 99/65314. Compounds of formula Ic are described in U.S. Pat. No. 5,656,573. Compound of formula Id is described in The Pesticide Manual $12^{th}$ ed., under Entry No. 71, compound of formula Ie under Entry No. 663 and compound of formula If under Entry No. 666. The compound of formula Ig (is described in Chemical Abstracts under the registration number CAS 192708-91-1. The compound of formula Ih is described in EP-A-0352543. The compound of formula II is described in EP-A-0 496 631, the compound of formula Ij in WO 04/021788. The compound of formula Ik (has the Chemical Abstracts registration number 365400-11-9.

In one aspect, the method according to the present invention is used to protect soya crops from the herbicidal injury of HPPD inhibitor herbicides of the classes of HPPD chemistry selected from the group consisting of the compounds of formula Ia or Ig. In an alternative aspect the cytochrome P450 gene is selected from a polynucleotide sequence encoding the amino acid sequence of SEQ ID NO:1 and SEQ ID NO:5. In a further embodiment the HPPD inhibitor herbicide is selected from sulcotrione, mesotrione, tembotrione and compounds of formula Ia where X is nitrogen and $R_4$ is $CF_3$, $CF_2H$ or $CFH_2$ and/or where $R_1$ and $R_2$ together form an ethylene bridge. In a further embodiment the HPPD inhibitor herbicide is selected from Mesotrione, SYN449280, Isoxaflutole, Tembotrione, Topramezone, Pyrasulfatole, Sulcotrione, Pyrazolynate, Pyrazoxyfen, Isoxachlortole, Benzofenap, and Benzobicyclon.

In another aspect soybean or other dicot crop plants are transformed to express both the cytochrome P450 gene encoding the amino acid sequence of SEQ ID NO: 1 or SEQ ID NO:5 and also an HPPD gene, which is derived from a monocot plant, for example from Avena, at sufficient levels to provide commercially useful levels of resistance to herbicides selected from sulcotrione, mesotrione, tembotrione and compounds of formula Ia where X is nitrogen and $R_4$ is $CF_3$, $CF_2H$ or $CFH_2$ and/or where $R_1$ and $R_2$ together form an ethylene bridge. The level of expression of the cytochrome P450 should be sufficient to reduce substantially (relative to likewise treated plants but lacking the P450 transgenes) the residue level of parent herbicide throughout the plant tissue and especially in the beans. One of ordinary skill in the art will of course understand that certain P450 enzymes are likely to confer resistance to certain subgroups of HPPD chemistry, and one enzyme may not provide resistance to all HPPDs.

In another embodiment, the present invention provides transgenic plants that are resistant or tolerant to herbicides selected from the group consisting of Benzothiadiazinones, Sulfonylureas, and other classes of herbicides including, for example, Imidazolinones, Triazolopyrimidines, Pyrimidinylthiobenzoates, Triazolinones, Auxins, Acetyl-coenzyme A Carboxylase (ACCase) inhibitors, Photosystem II (PSII) inhibitors, Protoporphyrinogen Oxidase (PPO) inhibitors, Phytoene Desaturase (PDS) inhibitors, Dinitroanalines, and Acetamides, as well as herbicides with unknown modes of action such as Difenzoquat and Clomazone.

Exemplary Benzothiadiazinones include Bentazon (CAS Registry No. 25057-89-0; available from BASF, Research Triangle Park, N.C.).

Exemplary Sulfonylureas include Bensulfuron (CAS Registry No. 99283-01-9), Chlorsulfuron (CAS Registry No. 64902-72-3), Halosulfuron (CAS Registry No. 135397-30-7), Nicosulfuron (CAS Registry No. 111991-09-4), Rimsulfuron (CAS Registry No. 122931-48-0), Sulfometuron (CAS Registry No. 74223-56-6), and Triflusulfuron (CAS Registry No. 135990-29-3), as well as salts and esters thereof. Additional Sulfonylureas include, but are not limited to, Trifloxysulfuron, Primisulfuron, Chlorimuron-ethyl, Amidosulfuron, Azimsulfuron, Bensulfuron-methyl, Cyclosulfamuron, Ethametsulfuron-methyl, Ethoxysulfuron, Flazasulfuron, Flupyrsulfuron-methyl, Halosulfuron-methyl, Imazosulfuron, Iodosulfuron, Metsulfuron-methyl, Foramsulfuron, Oxasulfuron, Prosulfuron, Pyrazosulfuron-ethyl, Sulfometuron-methyl, Sulfosulfuron, Tritosulfuron, Thifensulfuron-methyl, Triasulfuron, Tribenuron-methyl, and Triflusulfuron-methyl.

Exemplary Imidazolinones include, but are not limited to, Imazamox, Imazethapyr, Imazapic, Imazamethabenz-methyl, and Imazaquin.

Exemplary Triazolopyrimidines include, but are not limited to, Flumetsulam, Diclosulam, Florasulam, Chloransulam-methyl, and Metosulam.

Exemplary Pyrimidinylthiobenzoates include, but are not limited to, Bispyribac, Pyrithiobac, Pyriminobac-methyl, Pyriftalid, and Pyribenzoxim.

Exemplary Triazolinones include, but are not limited to, Flucarbazone, Thiencarbazone-methyl, and Propoxycarbazone.

Exemplary Auxins include, but are not limited to, Dicamba, Aminopyralid, 2,4-D, Mecoprop, Aminocyclopyrachlor, Quinclorac, Dichlorprop, MCPA, MCPB, 2,4-DB, Clopyralid, and Picloram.

Exemplary ACCase inhibitors include, but are not limited to, Fluazifop-P-butyl, Pinoxaden, Clodinafop-propargyl, Fenoxaprop-P-ethyl, Tralkoxydim, Diclofop-methyl, Cyhalofop-butyl, Haloxyfop-P-methyl, Quizalofop-P-ethyl, Alloxydim, Butroxydim, Clethodim, and Cycloxydim.

Exemplary PSII inhibitors include, but are not limited to, Bentazon, Linuron, Hexazinone, Metribuzin, Atrazine, Diuron, Isoproturon, Monolinuron, Desmedipham, Metamitron, Propanil, Amicarbzone, Fluometuron, Phenmedipham, Pyridate, Ametryn, Cynazine, Dimefuron, Fluometuron, Methibenzuron, Metoxuron, Prometryn, Simazine, Simetryn, Terbacil, Terbuthylazine, Chlorotoluron, and Trietazine.

Exemplary PPO inhibitors include, but are not limited to, Butafenacil, Fomesafen, Carfentrazone, Saflufenacil, Oxyfluorfen, Flumioxazin, Sulfentrazone, Lactofen, Oxadiazon, Acifluorfen, Flufenpyr-ethyl, Flumiclorac, and Oxadiargyl.

Exemplary PDS inhibitors include, but are not limited to, Norflurazon, Diflufenican, Fluorochloridone, Flurtamone, Picolinafen, and Fluridone.

Exemplary Dinitroanalines include, but are not limited to, Pendimethalin, Trifluralin, Orazalin, Butralin, Dinitroamine, and Ethalfluralin.

Exemplary Acetamides include, but are not limited to, Acetochlor, S-metolachlor, metolachlor, Dimethenamid, P-dimethenamid, Flufenacet, Alachlor, Butachlor, Mefenacet, Pretilachlor, Propachlor, and Thenylchlor.

In another embodiment, the present invention provides transgenic plants that are resistant or tolerant to herbicides selected from the group consisting of imidazolinones, triazolopyrimidines, pyrimidinyl(thio)benzoates, benzoic acids, phenoxycarboxylic acids, quinoline carboxylic acids, aryloxyphenoxypropionates, cyclohexanediones, dinitroani lines, benzamides, carbamates, ureas, amides, triazinones, phenylpyridazines, phenylcarbamates, triazolinones, pyrimidindiones, oxadiazoles, N-phenyl phthalimides, chloroacetamides, pyridazinones, and pyridinecarboxamides.

The present invention further provides a method of selectively controlling weeds at a locus comprising crop plants and weeds, wherein the plants are obtained by any of the methods of the current invention described above, wherein the method comprises application to the locus of a weed controlling amount of one or more herbicides. Any of the transgenic plants described herein may be used within these methods of the invention. The term "locus" may include soil, seeds, and seedlings, as well as established vegetation. Herbicides can suitably be applied pre-emergence or post-emergence.

The term "weed controlling amount" is meant include functionally, an amount of herbicide which is capable of affecting the growth or development of a given weed. Thus, the amount may be small enough to simply retard or suppress the growth or development of a given weed, or the amount may be large enough to irreversibly destroy a given weed.

Thus, the present invention provides a method of controlling weeds at a locus comprising applying to the locus a weed-controlling amount of one or more herbicides, where the locus comprises a transgenic plant that has been transformed with a nucleic acid molecule encoding a cytochrome P450 or variant thereof that confers resistance or tolerance to herbicides, alone or in combination with one or more additional nucleic acid molecules encoding polypeptides that confer desirable traits. In particular, the locus comprises a transgenic plant that has been transformed with a nucleic acid molecule encoding a cytochrome P450 or variant thereof that confers resistance or tolerance to an herbicide selected from the group consisting of HPPD inhibitors, Benzothiadiazinones, Sulfonylureas, Imidazolinones, Triazolopyrimidines, Pyrimidinylthiobenzoates, Triazolinones, Auxins, ACCase inhibitors, PSII inhibitors, PPO inhibitors, PDS inhibitors, Dinitroanalines, and Acetamides, as well as herbicides with unknown modes of action such as Difenzoquat and Clomazone. In another embodiment, the desirable trait is resistance or tolerance to an herbicide, including, for example, herbicides selected from the group consisting of an HPPD inhibitor, glyphosate, and glufosinate. In another embodiment, the locus comprises a transgenic plant that has been transformed with any combination of nucleic acid molecules described above, including one or more nucleic acid molecules encoding a cytochrome P450 or variant thereof that confers resistance or tolerance to an herbicide in combination with at least one, at least two, at least three, or at least four additional nucleic acid molecules encoding polypeptides that confer desirable traits.

In one embodiment, the present invention provides transgenic plants and methods useful for the control of unwanted plant species in crop fields, wherein the crop plants are made resistant to HPPD chemistry by transformation with cytochrome P450 genes expressing enzymes that degrade the HPPD herbicides. Over-the-top application of HPPD herbicide in amounts capable of killing or impairing the growth of unwanted plant species (weed species, or, for example, carryover or "rogue" or "volunteer" crop plants in a field of soybean crop plants). The application may be pre- or post emergence of the crop plants or of the unwanted species, and may combine other herbicides to which the crop is naturally tolerant, or to which it is resistant via expression of one or more other transgenes. See, e.g., U.S. application publication number 2004/0058427; PCT application WO98/20144.

In another embodiment, the invention also relates to a method of protecting crop plants from herbicidal injury. In the cultivation of crop plants, especially on a commercial scale, correct crop rotation is crucially important for yield stability (the achievement of high yields of good quality over a long period) and for the economic success of an agronomic business. For example, across large areas of the main maize-growing regions of the USA (the "central corn belt"), soya is grown as the subsequent crop to maize in over 75% of cases. Selective weed control in maize crops is increasingly being carried out using HPPD inhibitor herbicides. Although that class of herbicides has excellent suitability for that purpose, it can result in agronomically unacceptable phytotoxic damage to the crop plants in subsequent crops, especially in subsequent soya crops, because certain soya varieties are sensitive to even very small residues of such HPPD inhibitor herbicides ("carry-over" damage). Accordingly, the herbicide resistant or tolerant plants of the invention are also useful for planting in a locus of any short term carry-over of herbicide from a previous application (e.g., by planting a transgenic plant of the invention in the year following application of an herbicide to reduce the risk of damage from soil residues of the herbicide).

The invention is made clearer through the following non-limiting examples. The following examples are offered by way of illustration and not by way of limitation.

EXPERIMENTAL

Example 1

Gene Cassettes Suitable for Engineering Tolerance to HPPD Herbicides and, in Particular Mesotrione, into Crop Plants For example a DNA construct is made which has 1) a cassette having an *Avena* HPPD gene as in SEQ ID NO:14 or SEQ ID NO:15, for example, encoding a protein of or at least 85% similar to SEQ ID NO:10, or a modified *Avena* HPPD gene (e.g., encoding the amino acid sequence set forth in SEQ ID NO:11, 12, or 13), as described above, under operable expression control of an upstream promoter, such as a tobacco, *Arabidopsis* or soybean small subunit of Rubisco promoter region including 5' untranslated leader sequence and a downstream nopaline synthase 3' terminator sequence adjacent to a second cassette 2) having a DNA sequence encoding the maize nsf1 or the rice CYP81A6 protein sequence (SEQ ID NO:1 or SEQ ID NO: 5) under operable control of an upstream *Arabidopsis* or soybean polyubiquitin promoter and 5' untranslated leader sequence and a downstream 3' terminator sequence from a histone gene (See FIG. 1). Optionally constructs include, transcriptional enhancer sequences (e.g. from the CMV35S promoter region) are upstream of one or other of the promoters and optionally, translational enhancers such as the TMV omega sequence are included ahead of the translational start. Suitable sequences and method to manipulate the DNA in order to make these constructs are well known in the art. Optionally they are partially or entirely made synthetically and pieced together by PCR and Restriction Enzyme and ligation reactions. The promoters can also be chimeric promoters, where 5' upstream promoter regions are fused to a TATA box, and enhancers. Examples of optimized genes are *Avena* HPPD gene (SEQ ID NO:14), "modified *Avena* HPPD gene" (SEQ ID NO:15), nsf1 (SEQ ID NO:2), and corn CYP72A1 (SEQ ID NO:4).

In further variants of the example the cytochrome P450 and/or *Avena* genes are obtained synthetically from GeneArt, codon optimised for expression in soybean and designed to have 5' NdeI and 3'BamHI restriction sites for cloning (which adds no extra amino acids). Optionally, the Nde1:BamH1 products are cloned into vector pMCJA which is a derivative of pMJB1 (described in WO 98/20144) modified only to comprise an Nde1 rather than an Nco1 site at the translation initiation codon site. pMJB1 is a PUC19 derived plasmid which contains the plant operable double enhanced CAMV35S promoter, a TMV omega translational enhancer and the NOS transcription terminator. A schematic of the plasmid is depicted in FIG. 2 of WO 98/20144. The expression cassette comprising, for example, the double enhanced 35S promoter, TMV omega leader, SEQ ID NO:1 cytochrome P450 coding sequence and nos 3' terminator is excised, for example as appropriate, using a HindIII/EcoR1 partial digest and cloned into similarly digested pBIN19 and transformed into *E. coli* TOP 10 competent cells. DNA recovered from the *E. coli* is then used to transform *Agrobacterium tumefaciens* LBA4404 and the transformed bacteria selected on rifampicin and kanamycin. For example tobacco tissue is then subjected to *Agrobacterium*-mediated transformation using textbook standard methods well described in the art. Transformed shoots are regenerated from kanamycin resistant callus. Shoots are rooted on MS agar containing kanamycin. Surviving rooted explants are re-rooted to provide approximately 30-50 kanamycin resistant transformed tobacco plants.

Example 2

Transformation of Tobacco with Test CYP Genes and Selection of Herbicide-Resistant Lines Candidate full length genes were synthesized, including useful restriction sites, and a translational enhancer sequence 5' to the start site. These gene cassettes were cloned downstream of the FMV promoter, and these gene cassettes were next cloned into transformation vectors containing either a bar or PPO selectable marker gene cassette.

Alternatively, candidate full length cyp genes obtained from maize or rice cDNA libraries are edited by PCR to include, for example, 5' Nco1 and 3' Kpn1 ends. This product is then ligated into pMJB1. pMJB1 is a pUC19 derived plasmid which contains the plant operable double enhanced CaMV35S promoter; a TMV omega enhancer and the NOS transcription terminator. A schematic representation of the resulting plasmid is shown in FIG. 2 of WO 98/20144. The expression cassette, comprising the double enhanced 35S promoter, TMV omega leader, 4-HPPD gene and nos terminator, is excised using Hind III/Eco R1 (partial Eco R1 digest) and cloned into similarly digested pBIN 19 plant transformation vector and transformed into *E. coli* TOP 10 competent cells.

Alternatively, double gene constructs designed as in example 1 are suitably designed with restriction ends and similarly cloned into the pBIN19 plant transformation vector and transformed into *E. coli* TOP 10 cells.

Plant transformation vectors with the appropriate P450 gene expression cassette are used to transform *Agrobacterium tumefaciens* LBA4404. Tobacco tissue is subjected to *Agrobacterium*-mediated transformation using methods well described in the art. Transformed shoots are regenerated from callus resistant to the selection agent (e.g., glufosinate, butafenacil, kanamycin). Shoots are rooted on MS agar containing the selection agent.

To determine tolerance of P450 transgenic explants (i.e. a leaf plus short segment of stem containing the auxiliary bud), these are placed into MS agar (+3% sucrose) containing various concentrations of mesotrione, from 0.02 to 2 ppm. In tobacco, for example, untransformed explants are fully bleached at 0.02 ppm. They do not recover following prolonged exposure to the herbicide. In these particular experiments, only the shoot that develops from the bud is bleached, the leaf on the explanted tissue remains green.

A number of the transgene PCR+ve transformed plants tolerate mesotrione with no indication of bleaching at the level which causes symptoms on wild-type tobacco. They root normally and are phenotypically indistinguishable from untransformed plants. A sub-set of the transformants is tolerant to concentrations of >0.1 ppm yielding plants looking normal and rooting well in the presence of herbicide. Some of the transformed plants can be initially bleached when subjected to the herbicide at the said higher concentrations, but on prolonged exposure they progressively "green up" and "recover". Alternatively, T1 plants from events expressing a P450 transgene can be sprayed with mesotrione at levels that cause bleaching on new growth of non-transformed plants, but no bleaching in transgenic plants expressing a P450 transgene.

Alternatively, HPPD sensitive corn plants can be transformed with expression vectors containing the putative HPPD herbicide degrading P450 genes, and a selectable marker gene. Events can be tested for enhanced tolerance to the HPPD inhibitors.

Alternatively, soybean plants can be transformed with expression vectors containing the putative HPPD herbicide degrading P450 genes, and a selectable marker gene. Events can be tested for enhanced tolerance to the HPPD inhibitors.

Example 3

Transformation of Soybean and Selection of Herbicide-Resistant Plants

Linear DNA suitable for use in bombardment-based plant transformation is produced by digesting a vector comprising the desired genes (e.g. as in Example 1). This desired fragment is then purified on an agarose gel and isolated using a Biotrap.

Optionally, the CYP, the HPPD gene or both together can provide the means of selection and identification of transgenic tissue. Optionally the gene for expression of CYP and, for example, *Avena sativa* HPPD can be present in the polynucleotide alongside other sequences which provide additional means of selection/identification of transformed tissue including, for example, the known genes which provide resistance to kanamycin, hygromycin, phosphinothricin, butafenacil or glyphosate. Alternatively these selectable marker sequences may be present on separate polynucleotides and a process of, for example, co-transformation and co-selection is used. Alternatively, rather than a selectable marker gene a scorable marker gene such as GUS may be used to identify transformed tissue. Soybean plant material can be suitably transformed and fertile plants regenerated by many methods which are well known to the skilled man. For example, fertile morphologically normal transgenic soybean plants may be obtained by 1) production of somatic embryogenic tissue from e.g. immature cotyledon, hypocotyl or other suitable tissue 2) transformation by particle bombardment or infection with *Agrobacterium* and 3) regeneration of plants. 'In one example, as described in U.S. Pat. No. 5,024,944, cotyledon tissue is excised from immature embryos of soybean, preferably with the embryonic axis removed, and cultured on hormone-containing medium so as to form somatic embryogenic plant material. This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin or herbicides such as phosphonothricin or glyphosate or, alternatively, selection may be based upon expression of a visualisable marker gene such as GUS. Alternatively target tissues for transformation comprise meristematic rather than somaclonal embryogenic tissue or, optionally, is flower or flower-forming tissue.

In one example, constructs are transformed into regenerable embryogenic soybean tissues using either biolistic type approaches (e.g. Santarem E R, Finer, J. J (1999) 'Transformation of soybean (*Glycine max* (L.) Merrill) using proliferative embryogenic tissue maintained on a semi-solid medium. In vitro Cellular and Developmental Biology-Plant 35, 451-455; U.S. Pat. No. 5,503,998, U.S. Pat. No. 5,830,728) or via infection with *Agrobacterium* (e.g. U.S. Pat. No. 5,024,944, U.S. Pat. No. 5,959,179).

Proliferative embryogenic tissue can, for example, be maintained on a semi-solid medium. Such tissue, is, for example obtained in the following way. Immature zygotic embryos which are 3-4 mm long are isolated from pods of, for example, *Glycine max* (L.) Merrill, 2-3 weeks after flower formation. Pods can be checked for the presence of embryos of the correct length and maturity by 'backlighting'. Pods are then sterilized. Immature embryos are removed and the axis removed from each. Immature embryos are then plated on 'D40-Lite' semi-solid (0.2% gelrite) MS salts medium at pH 7.0 containing B5 vitamins, 3% sucrose and 40 mg/l 2,4-D for 3-4 weeks. For proliferation of embryos the material is then transferred to 'D20' MS salts medium at pH 5.7 containing B5 vitamins, 3% sucrose, 20 mg/l 2,4-D and 0.2% Gelrite. Material with bright green globular proliferative embryos is selected and subcultured every 2-3 weeks.

For bombardment, 20-25 clumps/plate of tissue are selected (subcultured 4-5 days prior to bombardment) and arranged in the centre of the dish containing D20 medium. The tissue is dried for 15 min by uncovering for 15 minutes under a sterile hood. Gold particles coated in DNA construct (coated, for example, using methods described in the references above) are twice bombarded into the tissue on D20 medium using any one of a large number of commercially available guns. By way of further example a PDS1000 particle gun is used. Particles may be prepared and coated with DNA in a similar manner to that described by Klein et al 1987, Nature, 327, 70-73. Alternatively, for example, 60 mg of gold or tungsten particles (~1.0 μm) in a microcentrifuge tube are washed repeatedly in HPLC-grade ethanol and then, repeatedly, in sterile water. The particles are resuspended in 1 ml of sterile water and dispensed into 50 μl aliquots in microcentrifuge tubes. Gold particles are stored at 4 C, tungsten particles at −20 C. 3 mg of DNA are added to each aliquot of (defrosted) particles and the tubes are vortexed at top speed. Whilst maintaining near continuous vortexing, 50 μl of 2.5M $CaCl_2$ and 20 μl of 0.1M spermidine is added. After 10 minutes of further vortexing, samples are centrifuged for 5 seconds in an eppendorf microcentrifuge, the supernatant is drawn off and the particles washed in successive additions of HPLC-grade ethanol. The particles are thoroughly resuspended in 60 μl of ethanol and then dispensed in 10 μl aliquots onto the surface of each macrocarrier to be used in the PDS1000 particle gun. Components of the PDS1000 particle gun are surface sterilised by immersion in 70% ethanol and air-drying. Target plates prepared, as described above, with tissue arranged into an ~2.5 cm disc are placed 6 cm from the stopping screen. Suitably chosen rupture discs are then used for bombardment.

One week after bombardment, all tissue clumps are transferred onto D20 medium, buffered to pH 5.7, containing a suitable selective concentration of selecting agent (for example glyphosate between 0.05 and 10 mM in the case that glyphosate be used for selection and that a resistant EPSPS or GOX encoding gene is either present on the same transforming DNA as the gene expressing *Avena sativa* HPPD or, otherwise, is present in co-bombarded DNA). After an additional 3-4 weeks all tissue is transferred to fresh D20 medium containing a suitable increased concentration of selecting agent. After a further 3-4 weeks, living tissue is selected and subcultured on every 3-4 weeks in similar D20 medium containing selection agent. In the case that some other selectable marker than glyphosate is present then selections may be made as appropriate (e.g. using increasing concentrations of hygromycin). Alternatively, all selections are made using HPPD inhibitor herbicides. Growing sections are thus maintained and, given enough tissue, may be analysed by PCR to confirm that they are transgenic for the desired DNA.

In order to develop and mature embryos, tissue clumps are placed onto M6 medium which comprises MS salts at pH 5.7 containing B5 vitamins, 6% maltose and 0.2% gelrite. 6-9 clumps are placed in a tall dish at 23° C. After 3-4 weeks, embryos elongate and can be separated and transferred to another round of incubation on M6 medium. After 4-6 weeks, embryos are cream-coloured and ready for desiccation. 9 such cream-coloured embryos are placed in a dry Petri dish, sealed with parafilm and placed onto a shelf for 2-3 days. Embryos should be somewhat flaccid and not "crispy-crunchy".

Desiccated embryos can be germinated by plating onto OMS (growth regulator-free MS medium). Following germination which normally occurs within a week plants are transferred to larger boxes and, once there is sufficient root and shoot formation, thence to soil. To prevent fungal contamination it is advisable to wash OMS from the roots with distilled water. Plants may be kept and grown under high humidity and, initially, under 24 hour lighting. Plants may be grown until about 2 feet tall under 24 hour lighting and then encouraged to flower and form pods through a shift to a 16 hour lighting regime. Seeds are collected and progeny grown on, crossed and backcrossed into order to move the transgenes into the desired plant background using the normal methods of plant breeding. Plants are routinely analysed for the presence and expression of transgenes using the normal methods of molecular biology including analysis by PCR, Southern, Western, ELISA and enzyme assay techniques.

An *Agrobacterium*-based method for soybean transformation is as follows:

Isolation of seeds from seed pods of different developing stages: Soybean (*Glycine max* cultivar Jack, Williams 82 or S42H1) stock plants are grown in greenhouse under 16 hours of day light at 24° C. Pods at developing stages R5-R7 (with green to yellow pod color) are collected and sterilized by immersing in 70% ethyl alcohol for 30 second or in 20% Clorox bleach for 20 minutes. Sterilized pods are rinsed with sterile water for 4 times. Seeds are then isolated from sterilized pods by hands in gloves sprayed with 70% ethyl alcohol. The isolated seeds are rinsed 3-5 times with sterile water or further sterilized with 10% Clorox for ten minutes followed by rinsing with sterile water three times. Sterilized seeds are then used directly for preparing explants for *Agrobacterium*-mediated transformation.

Transformation vector and *Agrobacterium* strains: A binary vector containing the modified HPPD gene, or a P450 gene, with the prerequisite genetic elements needed for expression, is used for transformation. These vectors are introduced separately into *Agrobacterium tumefaciens* strain LB4404 or EHA101 using electroporation. Single bacterial colony containing each of these vectors is selected to confirm the presence of intact vector and used for further experiments. *Agrobacterium* culture is cultured on YP solid medium containing appropriate antibiotics and grown at 28° C. incubator. *Agrobacterium* is streaked onto fresh YP medium the day before the inoculation and grown in the 28° C. incubator. For plant transformation use *Agrobacterium* is collected from the plate using a disposable plastic inoculation loop and suspended in liquid infection medium such as SoyInf in a sterile 50 ml disposable polypropylene centrifugation tube. Shake the tube gently until *Agrobacterium* cells are uniformly dispersed in the suspension. The bacterial cell suspension is then diluted to $A_{660}$ of 0.5 to 0.8 and acetosyringone is added to a final concentration of 40-80 mg/L (200-400 uM) to induce virulence gene expression.

Preparation of Transformation Targets: Explants are Prepared from Sterilized soybean seeds isolated directly from pods as described in Example 1 without further germination or culture in one of the following ways:
a) The hypocotyl is trimmed off just below the cotyledon nodes and the seed coat is removed. One cotyledon and two primary leaves are removed by breaking the adjacent tissue with the blunt end of the scalpel.
b) The hypocotyl is trimmed off just below the cotyledon nodes and the seed coat is removed. One cotyledon and two primary leaves are removed by breaking the adjacent tissue with the blunt end of the scalpel, and then the plumule including the apical meristem is wounded with the sharp end of blade.
c) The seed is cut longitudinally into two halves in the middle of the embryo axis. Both primary leaves are removed and then the apical region of the explant is further wounded with the sharp end of the scalpel. Both halves of the resulting explants include one cotyledon and part of the immature embryo axis.

Infection and Co-cultivation of soybean Seed Explants: The explants prepared as above Example 1.3 are infected with *Agrobacterium* by mixing the explants with bacterial suspension as prepared in Example 1.2. The mixture is incubated for 30 minutes to 4 hours at room temperature. Following infection, the explants are removed from the *Agrobacterium* suspension and placed on a co-cultivation medium such as SoyCoC. The co-cultivation plates were incubated for 3-5 days.

Regeneration and Selection of Transgenic Plants: After co-cultivation, elongated hypocotyls of the explants are trimmed back just below the cotyledon nodes. The explants are transferred on to recovery medium with antibiotics to kill *Agrobacterium* or inhibit *Agrobacterium* growth and with low or no selection agent, such as SoyR1. The plates with the explants are incubated, preferably for one week at 24° C. under 16 hours light/8 hours dark regimen, and >80 $\mu E/m^2/s$. After the recovery period, elongated epicotyls or developing shoots are excised and transferred to regeneration media with higher concentration of selection agent, such as SoyR2, along with the cotyledon for two weeks. SoyR2 medium contained 6-8 mg/L glufosinate for selection. After 2 weeks in regeneration/selection media such as SoyR2, developed or developing multiple shoots clusters are excised and transferred to elongation medium, such as SoyE1 for shoot elongation. SoyE1 contained 4-8 mg/L glufosinate. Subcultures to fresh elongation media are performed every two weeks. Elongated shoots (>2 cm) are transferred to elongation media SoyE2 without selection for two weeks. After two weeks in SoyE2 medium, shoots are transferred to a rooting medium, for example SoyRoot. Leaves were sampled for Taqman® analysis to identify transformants that contain bar or pat gene. Taqman® positive and rooted plantlets are rinsed with water to wash off the agar medium and transplanted to soil and grown in green house for seeds.

The following tables provide transformation media recipes used within the methods described herein:

TABLE 2

SoyInf medium.

| Recipe Name | SoyInf | | |
|---|---|---|---|
| Final pH | 5.4 | | |
| Recipe for 1 L | Name of Chemical | Amount | Units |
| | MS Basal Salt Mixture | 2.15 | g |
| | B5 Vitamins 200X | 5 | ml |
| | Sucrose | 20 | g |
| | Glucose | 10 | g |
| | MES | 4 | g |
| | Zeatin Riboside, Trans Isomers 1 mg/ml | 2 | ml |

TABLE 3

SoyCCM medium.

| Recipe Name | SoyCCM | | |
|---|---|---|---|
| Final pH | 5.4 | | |
| Recipe for 1 L | Name of Chemical | Amount | Units |
| | Sucrose | 20 | g |
| | MES | 4 | g |
| | Purified Agar | 6 | g |
| | Evian Water | 990 | ml |
| | Acetosyringone 40 mg/ml | 1 | ml |
| | BAP 1 mg/ml | 0.5 | ml |

TABLE 4

SoyCoC medium.

| Recipe Name | SoyCoC | | |
|---|---|---|---|
| Final pH | 5.4 | | |
| Recipe for 1 L | Name of Chemical | Amount | Units |
| | MS Basal Salt Mixture | 2.15 | g |
| | B5 Vitamins 200X | 5 | ml |
| | Sucrose | 20 | g |

TABLE 4-continued

SoyCoC medium.

Recipe Name: SoyCoC
Final pH: 5.4
Recipe for 1 L

| Name of Chemical | Amount | Units |
|---|---|---|
| Glucose | 10 | g |
| MES | 4 | g |
| Zeatin Riboside, Trans Isomers 1 mg/ml | 2 | ml |
| Purified Agar | 6 | g |

TABLE 5

SoyR1 medium.

Recipe Name: SoyR1
Final pH: 5.6
Recipe for 1 L

| Name of Chemical | Amount | Units |
|---|---|---|
| B5 Basal Salt, Gamborg's | 3.1 | g |
| B5 Vitamins 200X | 5 | ml |
| MS Iron 200X | 4 | ml |
| Asparagine | 100 | mg |
| MES 100 mg/ml | 10 | ml |
| Zeatin Riboside, Trans Isomers 1 mg/ml | 2 | ml |
| Sucrose | 30 | g |
| Purified Agar | 7 | g |
| Glutamine 50 mg/ml | 2 | ml |
| Ticarcillin:Potassium Clavulanate 15:1 100 mg/ml | 3 | ml |

TABLE 6

SoyR2 medium.

Recipe Name: SoyR2
Final pH: 5.6
Recipe for 1 L

| Name of Chemical | Amount | Units |
|---|---|---|
| B5 Basal Salt, Gamborg's | 3.1 | g |
| B5 Vitamins 200X | 5 | ml |
| MS Iron 200X | 4 | ml |
| Asparagine | 100 | mg |
| MES 100 mg/ml | 10 | ml |
| BAP 1 mg/ml | 1 | ml |
| Sucrose | 30 | g |
| Purified Agar | 7 | g |
| Glutamine 50 mg/ml | 2 | ml |
| Glufosinate ammonium | | |
| Ticarcillin:Potassium Clavulanate 15:1 100 mg/ml | 3 | ml |

TABLE 7

SoyE1 medium.

Recipe Name: SoyE1
Final pH: 5.6
Recipe for 1 L

| Name of Chemical | Amount | Units |
|---|---|---|
| MS Basal Salt Mixture | 4.3 | g |
| B5 Vitamins 200X | 5 | ml |
| MS Iron 200X | 3 | ml |
| Sucrose | 30 | g |
| MES | 590 | mg |
| Purified Agar | 7 | g |
| Ticarcillin:Potassium Clavulanate 15:1 100 mg/ml | 3 | ml |
| Cefotaxime 250 mg/ml | 0.4 | ml |
| Glufosinate ammonium | | mg |
| IAA 1 mg/ml | 0.1 | ml |

TABLE 7-continued

SoyE1 medium.

Recipe Name: SoyE1
Final pH: 5.6
Recipe for 1 L

| Name of Chemical | Amount | Units |
|---|---|---|
| GA3 5 mg/ml | 0.1 | ml |
| Glutamine 50 mg/ml | 2 | ml |
| Asparagine 25 mg/ml | 2 | ml |
| Zeatin Riboside, Trans Isomers 1 mg/ml | 1 | ml |

TABLE 8

SoyE2 medium.

Recipe Name: SoyE2
Final pH: 5.4
Recipe for 1 L

| Name of Chemical | Amount | Units |
|---|---|---|
| MS Basal Salt Mixture | 4.3 | g |
| B5 Vitamins 200X | 5 | ml |
| MS Iron 200X | 3 | ml |
| Sucrose | 30 | g |
| MES | 590 | mg |
| Gelrite | 3 | g |
| Ticarcillin:Potassium Clavulanate 15:1 100 mg/ml | 3 | ml |
| Cefotaxime 250 mg/ml | 0.4 | ml |
| Glufosinate ammonium | | mg |
| Glutamine 50 mg/ml | 2 | ml |
| Asparagine 25 mg/ml | 2 | ml |

TABLE 9

Soy Root medium.

Recipe Name: SoyRoot-H
Final pH: 5.4
Recipe for 1 L

| Name of Chemical | Amount | Units |
|---|---|---|
| MS Basal Salt Mixture | 2.2 | g |
| B5 Vitamins 200X | 5 | ml |
| MS Iron 200X | 3 | ml |
| Sucrose | 20 | g |
| MES | 590 | mg |
| Gelrite | 3 | g |
| Glutamine 50 mg/ml | 2 | ml |
| Asparagine 25 mg/ml | 2 | ml |
| IBA 1 mg/ml | 0.6 | ml |

Example 4

Construction of a Soybean Transformation Vector

Figure 3:
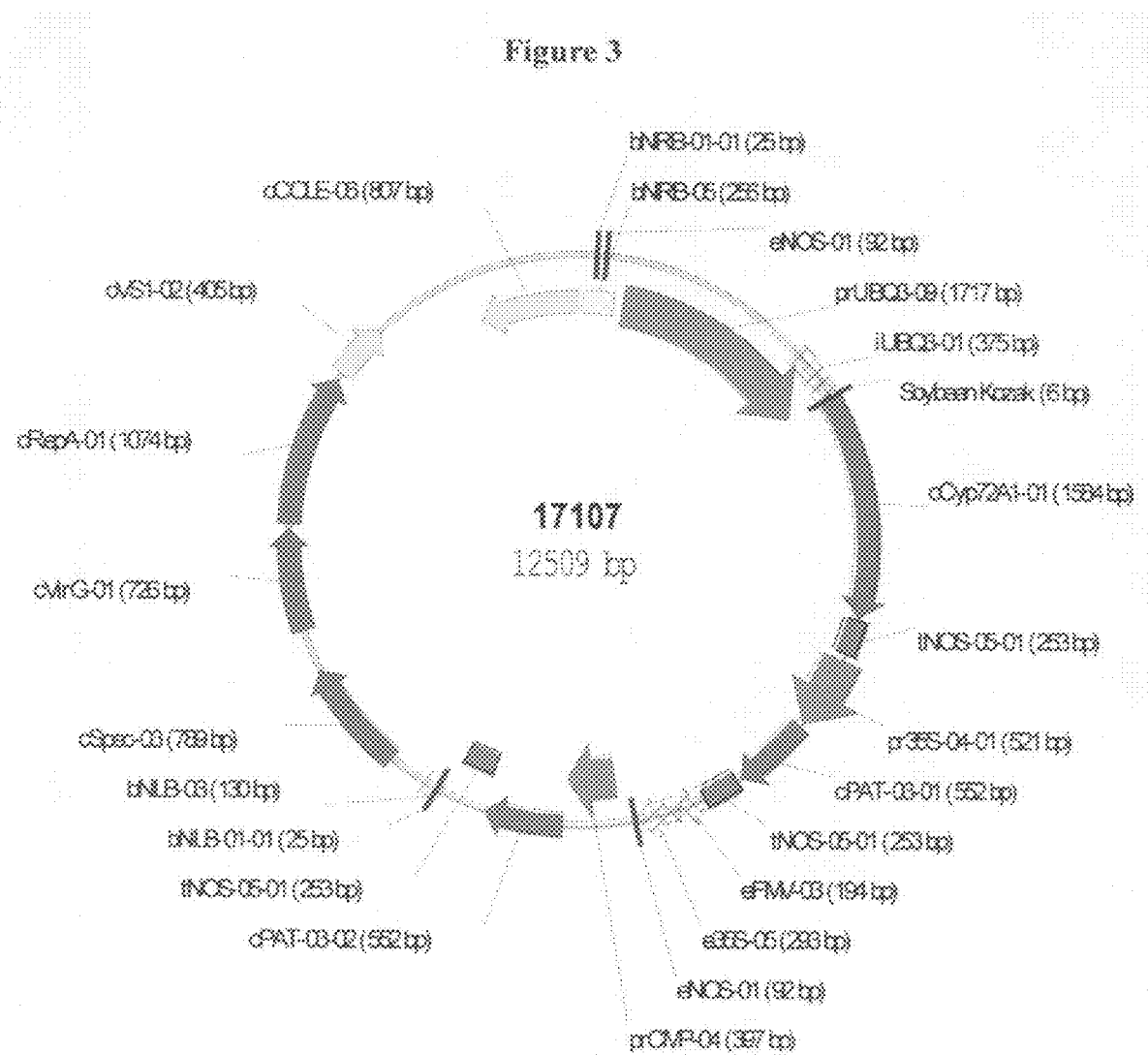
FIG. 3 shows a map of binary vector 17107 harbouring the CYP72A 1 coding region.

A binary vector (17107) for dicot (soybean) transformation was constructed, with the *Arabidopsis* UBQ3 promoter driving the corn CYP72A1 cytochrome P450 gene, followed by NOS terminator (FIG. 3). The gene was codon optimized for soybean expression based upon the predicted amino acid sequence of the maize gene coding region. The amino acid sequence of the protein encoded by the CYP72A1 gene is provided in SEQ ID NO:3, and the nucleotide sequence of the optimized CYP72A1 gene in this binary transformation vector is provided in SEQ ID NO:4. The transformation vector also contains two PAT gene cassettes (one with the 35S promoter and one with the CMP promoter, and both PAT genes are followed by the nos terminator) for glufosinate based selection during the transformation process.

Figure 4:
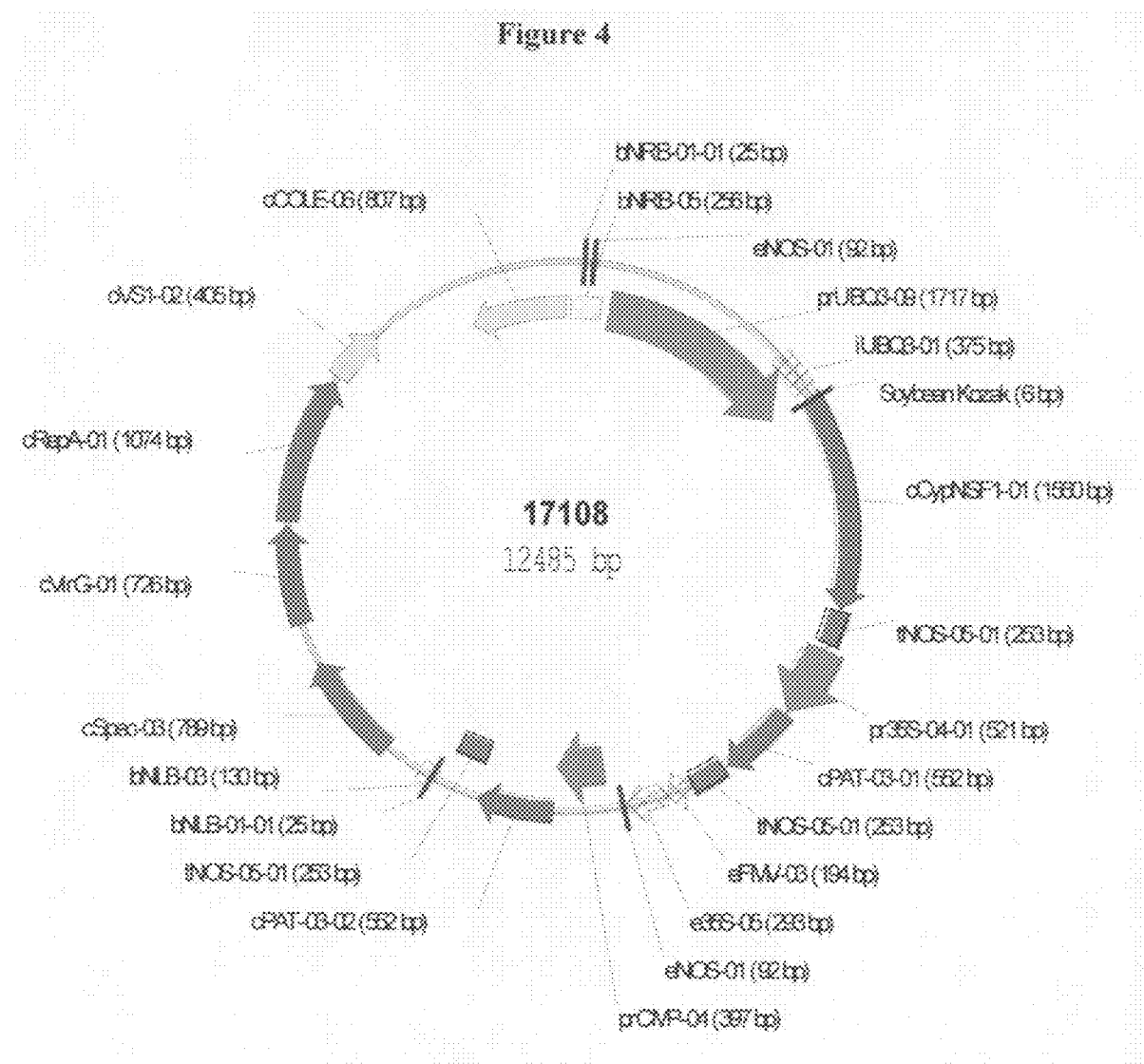
FIG. 4 shows a map of binary vector 17108 harbouring the NSF coding region.

A similar binary vector (17108) was constructed with the corn cytochrome P450 gene 'nsf' instead of the CYP72A1 gene (FIG. 4). The nsf gene in this vector was codon optimized for soybean expression (SEQ ID NO:2) based upon the predicted amino acid sequence of the maize gene coding region (SEQ ID NO:1).

Example 5

Soybean Transformation

Transformed Soybean plants were generated with each of the CYP vectors described in Example 4. These events were created using the *Agrobacterium* method described in Example 3 (see also U.S. patent application Ser. No. 11/716,975).

Example 6

T0 Plant Establishment and Selection

T0 plants were taken from tissue culture to the greenhouse where they are transplanted into saturated soil (Redi-Earth® Plug and Seedling Mix, Sun Gro Horticulture, Bellevue, Wash.) mixed with 1% granular Marathon® (Olympic Horticultural Products, Co., Mainland, Pa.) at 5-10 g/gal Redi-Earth® Mix in 2" square pots. The plants were covered with humidity domes and placed in a Conviron chamber (Pembina, N. Dak.) with the following environmental conditions: 24° C. day; 18° C. night; 23 hr photoperiod; 80% relative humidity. After plants became established in the soil and new growth appeared (~1-2 weeks), plants were sampled and tested for the presence of desired transgene by Taqman® analysis using probes for P450 (CYP72A1), or promoters (prCMP and prUBq3). All positive plants and several negative plants were transplanted into 4" square pots containing MetroMix® 380 soil (Sun Gro Horticulture, Bellevue, Wash.). Sierra 17-6-12 slow release fertilizer was incorporated into the soil at the recommended rate. The negative plants serve as controls for the spray experiment. The plants were then relocated into a standard greenhouse to acclimatize (~1 week). The environmental conditions were: 27° C. day; 21° C. night; 12 hr photoperiod (with ambient light); ambient humidity. After acclimatizing (~1 week), the plants were ready to be sprayed with the desired herbicides.

Example 7

Plant Treatment and Evaluation

The plants from Example 6 were sprayed with mesotrione to determine if they were tolerant to this herbicide. Callisto® (active ingredient mesotrione, Syngenta Crop Protection, Inc., Greensboro, N.C.) was mixed in water and X-77 surfactant (0.25% v/v final concentration). Plants were placed in a DeVries spray chamber (DeVries Manufacturing, Hollandale, Minn.), and the distance from the nozzle to the top of the plants was adjusted to approximately 12 inches. The system was set up so that the boom moved at 2 mph, and delivered 25 gallon fluid per acre. The spray rate was calibrated to spray 52.5 g/ha mesotrione over the top of the plants. Negative T0 transformants (i.e., negative by Taqman® for presence of transgenes), T0 transformants with vector 17107, and one transformant with vector 17108 (event 17108-A), were sprayed in this manner. After spraying, plants were placed in the greenhouse, under the same conditions as described in Example 3 above, and evaluated frequently for symptoms. All plants that were sprayed developed necrotic symptoms on small portions of the leaves that were exposed at the time of herbicide application. New growth that emerged from the plants was completely bleached on all plants. However, over time, leaves greened up on all plants. New growth developed as partially bleached, or chlorotic, and the leaves that initially were bleached also greened up. At 1 week after spray, it was clear that the leaves of event 17108-A turned green faster than the leaves on events with vector 17107. At 22 days after the spray, the plants were rated for symptoms on the leaves that were initially bleached. Visible chlorosis was only seen on the leaves immediately above the leaves that were exposed during the spray (i.e., the leaves that had necrotic spots), and in some events, on leaves in sideshoots. The partial chlorosis was evident as light green patches, and often as light green (almost yellow) edges on the leaves. This data is shown in Table 10 below.

TABLE 10

Evaluation of plants following mesotrione treatment.

| Event number | Genotype, as determined by Taqman® | Number of leaves with ≧50% chlorosis | Number of leaves with <50% chlorisis |
|---|---|---|---|
| 6D032-A #4 | Negative | 1 | 1 |
| 6D032-A #14 | Negative | 2 | 0 |
| 17107-A | 17107 positive | 2 | 0 |
| 17107-B | 17107 positive | 2 | 2 |
| 17107-C | 17107 positive | 1 | 1 |
| 17107-D | 17107 positive | 3 | 2 |
| 17107-E | 17107 positive | 2 | 1 |
| 17107-F | 17107 positive | 1 | 2 |
| 17107-G | 17107 positive | 1 | 2 |
| 17107-H | 17107 positive | 2 | 4 |
| 17107-I | 17107 positive | 1 | 1 |
| 17108-A | 17108 positive | 0 | 0 |

As shown above, only event 17108-A containing the nsf P450 gene was able to fully recover from the mesotrione injury.

Example 8

Analysis of T1 Seed from 17108 Events for HPPD Herbicide Tolerance

T0 transformants containing the nsf transgene (vector 17108) are allowed to set T1 seed, and the seed is harvested. This seed is planted, and the progeny analyzed to identify seedlots that are derived from germline transformed plants. Transgenic progeny plants (T1 or later generations), are analyzed to confirm mesotrione tolerance. Plants grown from the progeny seeds also display tolerance when sprayed with other HPPD herbicides (including but not limited to Tembotrione, Isoxaflutole, Topramezone, Pyrasulfatole, Sulcotrione, Pyrazolynate, Pyrazoxyfen, Isoxachlortole, Benzofenap, and Benzobicyclon). The plants are sprayed at 40-80 g/ha rates with these herbicides, or rates higher than this, as described in Example 7. Plants are evaluated for bleaching, and chlorosis, as described in Example 7.

Example 9

Ability of P450 Expressing Plants to Degrade Other Herbicides

A number of plants have the ability to degrade herbicides via a P450-based degradation mechanism, and it is generally assumed that this degradation is partly or primarily responsible for the herbicide tolerance of these plants. One example is the ability of the corn CYP72A1 enzyme to degrade the herbicides bentazon, chlortoluron, and chlorimuron. In addition, these plants are also able to degrade the insecticide malathion (see, e.g., U.S. Pat. No. 6,380,465). Likewise, the nsf enzyme has been shown to confer tolerance to a range of herbicides including HPPD herbicides, certain sulfonylureas, certain PPO herbicides, and other classes of herbicides (see, e.g., U.S. Patent Application No. 2007/0214515 A1). Another example is the rice CYP81A6 enzyme, that is able to degrade bentazon and certain sulfonyl urea herbicides (Pan et al. (2007) *Plant Molecular Biology*, 61:933-943). Consequently, when the P450s described herein are expressed at appropriate levels in plants, they may provide tolerance to a variety of herbicides, including Benzothiadiazinones, Sulfonylureas, Imidazolinones, Triazolopyrimidines, Pyrimidinylthiobenzoates, Triazolinones, Auxins, Acetyl-coenzyme A Carboxylase (ACCase) inhibitors, Photosystem II (PSII) inhibitors, Protoporphyrinogen Oxidase (PPO) inhibitors, Phytoene Desaturase (PDS) inhibitors, Dinitroanalines, and Acetamides, as well as herbicides with unknown modes of action such as Difenzoquat and Clomazone.

In the Benzothiadiazinone herbicide class, P450 enzymes may degrade herbicides that include, but are not limited to, Bentazon.

In the Sulfonylurea herbicide class, P450 enzymes may degrade herbicides that include, but are not limited to, Nicosulfuron, Trifloxysulfuron and Rimsulfuron, and may also degrade Primisulfuron, Chlorimuron-ethyl, Amidosulfuron, Azimsulfuron, Bensulfuron-methyl, Chlorsulfuron, Cyclosulfamuron, Ethametsulfuron-methyl, Ethoxysulfuron, Flazasulfuron, Flupyrsulfuron-methyl, Halosulfuron-methyl, Imazosulfuron, Iodosulfuron, Metsulfuron-methyl, Foramsulfuron, Oxasulfuron, Prosulfuron, Pyrazosulfuron-ethyl, Sulfometuron-methyl, Sulfosulfuron, Tritosulfuron, Thifensulfuron-methyl, Triasulfuron, Tribenuron-methyl, and Triflusulfuron-methyl.

In the Imidazolinone herbicide class, P450 enzymes may degrade herbicides that include, but are not limited to, Imazamox, Imazethapyr, Imazapic, Imazamethabenz-methyl, and Imazaquin.

In the Triazolopyrimidines herbicide class, P450 enzymes may degrade herbicides that include, but are not limited to, Flumetsulam, Diclosulam, Florasulam, Chloransulam-methyl, and Metosulam.

In the Pyrimidinylthiobenzoates herbicide class, P450 enzymes may degrade herbicides that include, but are not limited to, Bispyribac, Pyrithiobac, Pyriminobac-methyl, Pyriftalid, and Pyribenzoxim.

In the Triazolinones herbicide class, P450 enzymes may degrade herbicides that include, but are not limited to, Flucarbazone, Thiencarbazone-methyl, and Propoxycarbazone.

In the Auxin herbicide class, P450 enzymes may degrade herbicides that include, but are not limited to, Dicamba, Aminopyralid, 2,4-D, Mecoprop, Aminocyclopyrachlor, Quinclorac, Dichlorprop, MCPA, MCPB, 2,4-DB, Clopyralid, and Picloram.

In the ACCase inhibitor herbicide class, P450 enzymes may degrade herbicides that include, but are not limited to, Fluazifop-P-butyl, Pinoxaden, Clodinafop-propargyl, Fenoxaprop-P-ethyl, Tralkoxydim, Diclofop-methyl, Cyhalofop-butyl, Haloxyfop-P-methyl, Quizalofop-P-ethyl, Alloxydim, Butroxydim, Clethodim, and Cycloxydim.

In the PSII inhibitor herbicide class, P450 enzymes may degrade herbicides that include, but are not limited to, Bentazon, Linuron, Hexazinone, Metribuzin, Atrazine, Diuron, Isoproturon, Monolinuron, Desmedipham, Metamitron, Propanil, Amicarbzone, Fluometuron, Phenmedipham, Pyridate, Ametryn, Cynazine, Dimefuron, Fluometuron, Methibenzuron, Metoxuron, Prometryn, Simazine, Simetryn, Terbacil, Terbuthylazine, Chlorotoluron, and Trietazine.

In the PPO inhibitor herbicide class P450 enzymes may degrade herbicides that include, but are not limited to, Butafenacil, Fomesafen, Carfentrazone, Saflufenacil, Oxyfluorfen, Flumioxazin, Sulfentrazone, Lactofen, Oxadiazon, Acifluorfen, Flufenpyr-ethyl, Flumiclorac, and Oxadiargyl.

In the PDS inhibitor herbicide class, P450 enzymes may degrade herbicides that include, but are not limited to, Norflurazon, Diflufenican, Fluorochloridone, Flurtamone, Picolinafen, and Fluridone In the Dinitroanalines herbicide class, P450 enzymes may degrade herbicides that include, but are not limited to, Pendimethalin, Trifluralin, Orazalin, Butralin, Dinitroamine, and Ethalfluralin.

In the Acetamides herbicide class, P450 enzymes may degrade herbicides that include, but are not limited to, Acetochlor, S-metolachlor, metolachlor, Dimethenamid, P-dimethenamid, Flufenacet, Alachlor, Butachlor, Mefenacet, Pretilachlor, Propachlor, and Thenylchlor.

In addition, P450 enzymes may degrade herbicides that include, but are not limited to, Difenzoquat and Clomazone, herbicides with unknown mode of action.

All publications, patents and patent applications are herein incorporated by reference to the same extent as if each individual publication, patent or patent application was specifically and individually indicated to be incorporated by reference.

That which is claimed:

1. A method of controlling weeds at a locus, said method comprising applying to said locus a weed-controlling amount of one or more herbicides, wherein said locus comprises a plant comprising a heterologous polynucleotide sequence encoding a cytochrome P450, wherein said polynucleotide sequence is selected from the group consisting of:
a) the nucleotide sequence set forth as nucleotides 123-1664 in SEQ ID NO: 6;
b) a nucleotide sequence encoding a polypeptide comprising the amino acid sequence set forth in SEQ ID NO: 5
wherein the one or more herbicides are selected from the group consisting of:
a) any HPPD inhibitor
b) the compounds of formula Ia

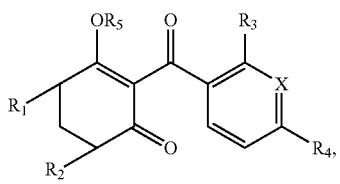

wherein X is nitrogen and $R_4$ is $CF_3$, $CF_2H$ or $CFH_2$ and/or $R_1$ and $R_2$ together form an ethylene bridge;

c) sulcotrione;
d) mesotrione;
e) tembotrione;
f) any PPO inhibitor;
g) saflufenacil;
h) butafenacil;
i) flumioxazin; and
j) sulfentrazone.

2. The method of claim 1, wherein said nucleic acid construct further comprises a second polynucleotide sequence encoding a polypeptide that confers a desirable trait.

3. The method of claim 2, wherein said desirable trait is resistance or tolerance to an herbicide selected from the group consisting of an HPPD inhibitor, glyphosate, and glufosinate.

4. The method according to claim 1, wherein the one or more herbicides is mesotrione.

5. The method of claim 1, wherein said plant is a rice, barley, potato, sweet potato, canola, sunflower, rye, oats, wheat, corn, soybean, sugar beet, tobacco, Miscanthus grass, Switch grass, safflower, trees, cotton, cassava, tomato, sorghum, alfalfa, sugar beet, or sugarcane plant.

6. The method of claim 5 wherein said plant is a soybean plant.

7. The method claim 1, wherein the one or more herbicides is saflufenacil.

* * * * *

SEQUENCE LISTING

```
<160> NUMBER OF SEQ ID NOS: 15

<210> SEQ ID NO 1
<211> LENGTH: 521
<212> TYPE: PRT
<213> ORGANISM: Zea mays

<400> SEQUENCE: 1

Met Asp Lys Ala Tyr Ile Ala Ala Leu Ser Ala Ala Ala Leu Phe Leu
1               5                   10                  15

Leu His Tyr Leu Leu Gly Arg Arg Ala Gly Gly Glu Gly Lys Ala Lys
            20                  25                  30

Ala Lys Gly Ser Arg Arg Arg Leu Pro Pro Ser Pro Pro Ala Ile Pro
```

-continued

```
                35                  40                  45
Phe Leu Gly His Leu His Leu Val Lys Ala Pro Phe His Gly Ala Leu
 50                  55                  60

Ala Arg Leu Ala Ala Arg His Gly Pro Val Phe Ser Met Arg Leu Gly
 65                  70                  75                  80

Thr Arg Arg Ala Val Val Ser Ser Pro Asp Cys Ala Arg Glu Cys
                 85                  90                  95

Phe Thr Glu His Asp Val Asn Phe Ala Asn Arg Pro Leu Phe Pro Ser
                100                 105                 110

Met Arg Leu Ala Ser Phe Asp Gly Ala Met Leu Ser Val Ser Ser Tyr
                115                 120                 125

Gly Pro Tyr Trp Arg Asn Leu Arg Arg Val Ala Ala Val Gln Leu Leu
                130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
                180                 185                 190

Ser Val Leu Met Glu Thr Ile Ala His Thr Lys Thr Ser Arg Ala Glu
                195                 200                 205

Ala Asp Ala Asp Ser Asp Met Ser Thr Glu Ala His Glu Phe Lys Gln
210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
                260                 265                 270

Asp Gly Glu Arg Arg Leu Asp Ala Gly Asp Glu Ser Glu Ser Lys
                275                 280                 285

Ser Met Ile Ala Val Leu Leu Thr Leu Gln Lys Ser Glu Pro Glu Val
290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
                340                 345                 350

Ala Val Gly Thr Ser Arg Leu Val Thr Ala Asp Asp Val Pro His Leu
                355                 360                 365

Thr Tyr Leu Gln Cys Ile Val Asp Glu Thr Leu Arg Leu His Pro Ala
                370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
                420                 425                 430

Glu Arg Phe Glu Gly Ala Gly Gly Lys Ala Glu Gly Arg Leu Leu Met
                435                 440                 445

Pro Phe Gly Met Gly Arg Arg Lys Cys Pro Gly Glu Thr Leu Ala Leu
450                 455                 460
```

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
            485                 490                 495

Thr Met Pro Arg Ala Val Pro Leu Glu Ala Met Cys Arg Pro Arg Thr
            500                 505                 510

Ala Met Arg Gly Val Leu Lys Arg Leu
            515                 520

<210> SEQ ID NO 2
<211> LENGTH: 1560
<212> TYPE: DNA
<213> ORGANISM: Artificial Sequence
<220> FEATURE:
<223> OTHER INFORMATION: Chemically Synthesized

<400> SEQUENCE: 2

```
atggacaagg cttacattgc tgctttgtct gctgctgctc ttttccttct tcactacctc    60
ttgggaagaa gagctggcgg agagggaaag gctaaggcta agggttctag aagaaggctt   120
ccaccatctc cacctgctat tccattcctt ggacacctct ccttgttaa ggctccattc    180
cacggtgctc ttgctagact tgctgctaga catggaccag tgttctctat gaggcttgga   240
actagaaggg ctgtggtggt ttcttctcca gattgcgcta gagagtgctt cactgagcac   300
gatgtgaact cgctaacag gccacttttc ccatctatga ggctcgcttc attcgatggt    360
gctatgcttt ctgtgtcctc ctatggacca tattggagga accttagaag agttgctgct   420
gttcagcttc tttctgctca tagagtggga tgtatggctc cagctattga ggctcaagtt   480
agggctatgg tgagaagaat ggatagagct gctgctgctg gcggaggtgg agttgctaga   540
gttcagctca agagaaggct tttcgagctt ccctttccg ttctcatgga aaccattgct    600
cacactaaga cttctagggc tgaggctgat gctgattctg atatgtctac cgaggctcat   660
gagttcaagc agatcgtgga tgagcttgtg ccttacattg aactgctaa cagatgggat    720
taccttccag tgctcagatg gttcgatgtt tcggagtga ggaacaagat tctcgatgct    780
gtgggaagaa gggatgcttt cctcggaagg cttattgatg cgagagaag aagattggac   840
gctggcgatg agtctgagtc caagtccatg attgctgtgc ttctcaccct tcaaaagtct   900
gagccagagg tttacaccga taccgtgatt accgctctta accttttcgg agctggaact   960
gagactactt ctactactac cgagtgggct atgtctcttc ttctcaacca cagagaggct  1020
cttaagaagg ctcaggctga gattgatgct gctgttggaa cctctaggct tgttaccgct  1080
gatgatgttc cacaccttac ctaccttcag tgcattgtgg atgagaccct tagacttcat  1140
ccagctgctc cactttttgct tccacatgag tctgctgctg attgcactgt ggaggatac   1200
gatgttccaa gggcactat gcttttggtt aacgtgcatg ctgttcacag agatccagct  1260
gtttgggaag atccagacag attcgttcca gagagattcg aaggcgcagg tgaaaagct   1320
gagggaaggc ttcttatgcc attcggaatg ggtagaagaa agtgcccagg tgaaactctt  1380
gctcttagga ctgtgggact tgttcttgct actctcctcc aatgcttcga ttgggatact  1440
gttgatggtg ctcaggttga catgaaggct tcaggtggac ttactatgcc aagggctgtt  1500
ccacttgagg ctatgtgcag accaagaact gctatgaggg gagtgcttaa gaggctttga  1560
```

<210> SEQ ID NO 3
<211> LENGTH: 527
<212> TYPE: PRT
<213> ORGANISM: Zea mays

-continued

<400> SEQUENCE: 3

```
Met Ala Thr Cys Asp Leu Leu Met Leu Arg Glu Ala Ser Pro Trp Ala
1               5                   10                  15

Leu Ala Gly Ala Val Ala Ser Val Ser Leu Leu Trp Leu Val Ala Trp
            20                  25                  30

Thr Leu Glu Trp Ala Trp Trp Thr Pro Trp Arg Leu Asp Arg Ala Leu
        35                  40                  45

Arg Ala Gln Gly Leu Asn Gly Thr Arg Tyr Arg Leu Phe Thr Gly Asp
    50                  55                  60

Leu Arg Glu Thr Ala Arg Val Asn Arg Glu Ala Arg Lys Lys Pro Leu
65                  70                  75                  80

Pro Leu Gly Cys His Asp Ile Thr Pro Arg Val Gln Pro Met His His
                85                  90                  95

Ser Thr Ile Lys Glu Tyr Gly Lys Leu Ser Phe Thr Trp Phe Gly Pro
            100                 105                 110

Thr Pro Arg Val Met Ile Pro Asp Pro Glu Leu Val Lys Glu Val Leu
        115                 120                 125

Ser Asn Lys Phe Gly His Phe Gly Lys Pro Arg Ser Ser Arg Ile Gly
    130                 135                 140

Arg Leu Leu Ala Asn Gly Leu Val Asn His Asp Gly Glu Lys Trp Ala
145                 150                 155                 160

Lys His Arg Arg Ile Leu Asn Pro Ala Phe His His Glu Lys Ile Lys
                165                 170                 175

Gly Met Met Pro Val Phe Ser Thr Cys Cys Ile Glu Met Ile Thr Arg
            180                 185                 190

Trp Asp Asn Ser Met Ser Ser Glu Gly Ser Ser Glu Ile Asp Val Trp
        195                 200                 205

Pro Glu Phe Gln Asn Leu Thr Gly Asp Val Ile Ser Arg Thr Ala Phe
    210                 215                 220

Gly Ser Asn Tyr Gln Glu Gly Arg Arg Ile Phe Glu Leu Gln Gly Glu
225                 230                 235                 240

Leu Ala Glu Arg Leu Ile Gln Ser Val Gln Thr Ile Phe Ile Pro Gly
                245                 250                 255

Tyr Trp Phe Leu Pro Thr Lys Asn Asn Arg Arg Met Arg Ala Ile Asp
            260                 265                 270

Val Glu Ile Arg Lys Ile Leu Arg Glu Ile Ile Gly Lys Arg Glu Lys
        275                 280                 285

Asp Thr Lys Asn Arg Glu Thr Asn Lys Asp Asp Leu Leu Gly Leu Leu
    290                 295                 300

Leu Glu Ser Asn Thr Arg Gln Ser Asn Gly Asn Ala Ser Leu Gly Leu
305                 310                 315                 320

Thr Thr Glu Asp Val Ile Glu Glu Cys Lys Leu Phe Tyr Phe Ala Gly
                325                 330                 335

Met Glu Thr Thr Ser Val Leu Leu Thr Trp Thr Leu Ile Val Leu Ser
            340                 345                 350

Met His Pro Glu Trp Gln Glu Arg Ala Arg Glu Glu Val Leu Ser His
        355                 360                 365

Phe Gly Arg Thr Thr Pro Asp Tyr Asp Ser Leu Ser Arg Leu Lys Thr
    370                 375                 380

Val Thr Met Ile Leu His Glu Val Leu Arg Leu Tyr Pro Pro Ala Thr
385                 390                 395                 400

Phe Leu Thr Arg Arg Thr Tyr Lys Glu Met Glu Leu Gly Gly Ile Lys
                405                 410                 415
```

```
Tyr Pro Ala Gly Val Glu Leu Leu Pro Val Ile Phe Ile His His
            420                 425                 430

Asp Pro Asp Ile Trp Gly Lys Asp Ala Ser Glu Phe Asn Pro Glu Arg
                435                 440                 445

Phe Ala Asn Gly Ile Ser Ser Ala Thr Arg His Gln Ala Ala Phe Phe
        450                 455                 460

Pro Phe Gly Gly Pro Arg Ile Cys Ile Gly Gln Ser Phe Ala Leu
465                 470                 475                 480

Leu Glu Ala Lys Met Thr Leu Cys Thr Ile Leu Gln Arg Phe Ser Phe
                485                 490                 495

Glu Leu Ser Pro Ser Tyr Thr His Ala Pro Tyr Thr Val Ile Thr Leu
            500                 505                 510

His Pro Gln His Gly Ala Gln Ile Arg Leu Lys Lys Leu Ser Pro
            515                 520                 525

<210> SEQ ID NO 4
<211> LENGTH: 1584
<212> TYPE: DNA
<213> ORGANISM: Artificial Sequence
<220> FEATURE:
<223> OTHER INFORMATION: Chemically Synthesized

<400> SEQUENCE: 4
atggctacct gcgatcttct tatgcttaga gaggcttctc cttgggctct tgctggtgct    60
gttgcttctg tgtctcttct ttggcttgtt gcttggactc ttgaatgggc ttggtggact   120
ccttggagac ttgatagggc tcttagggct caaggactta acggaaccag gtacaggctt   180
ttcactggtg atcttagaga accgctaggg ttaacagag aggctaggaa gaagccactt    240
ccacttggat gccacgatat tactccaagg gttcagccaa tgcaccactc taccatcaaa   300
gagtacggca agttgtcttt cacttggttt ggaccaactc caagggtgat gattccagat   360
ccagagcttg tgaaagaggt gctctccaac aagttcggac atttcggaaa gccaaggtcc   420
tctaggattg aaggcttct tgctaacgga cttgtgaacc atgatggcga agtgggct     480 aaacacagaa ggattctcaa cccagctttc caccacgaga gatcaagggg aatgatgcca   540
gttttctcca cttgctgcat cgagatgatc accagatggg ataactctat gtcctctgag   600
ggatcttctg agattgatgt gtggccagag ttccaaaacc ttaccggcga tgtgatttct   660
agaaccgctt tcggttccaa ctatcaagag ggcagaagga ttttcgagct tcaaggtgaa   720
cttgctgaga ggcttattca gtccgttcag accattttca tcccaggata ctggttcctt   780
cctaccaaga caacagaag gatgagggct attgatgtgg agatcaggaa gatcctcaga   840
gagattatcg gcaagagaga gaaggatacc aagaacagag agaccaacaa ggacgatctt   900
cttggacttc ttctcgagtc taacaccagg caatctaacg gaaacgcttc tcttggactt   960
actaccgagg atgtgatcga ggaatgcaag ctcttctact cgctggaat ggaaaccact   1020 tctgtgcttt tgacctggac ccttattgtg ctttctatgc acccagagtg gcaagaaaga   1080
gctagggaag aggttttgtc tcatttcgga aggactaccc cagattacga ttctcttttcc   1140 aggcttaaga ccgtgaccat gattcttcat gaggtgctca gacttatcc acctgctacc    1200 ttccttacta gaaggaccta caaagagatg gaactcggag gtattaagta cccagctggc   1260
gttgaacttc ttctcccagt gatcttcatt caccacgatc cagatatttg gggaaaggac   1320
gcttctgagt tcaacccaga gagattcgct aacggaattt cttctgctac taggcatcag   1380
gctgctttct ccccatttgg aggtggacca aggatctgca ttggacagtc tttcgctctt   1440
ctcgaggcta agatgacctt gtgcaccatt cttcagaggt tcagcttcga gctttctcca   1500
```

```
tcttacaccc atgctccata caccgttatt acccttcatc cacagcatgg tgctcagatt    1560
aggcttaaga agctctcccc ttga                                          1584
```

<210> SEQ ID NO 5
<211> LENGTH: 513
<212> TYPE: PRT
<213> ORGANISM: Oryza sativa

<400> SEQUENCE: 5

```
Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Pro Ala Val Pro Ile Leu Gly His Leu His Leu
        35                  40                  45

Val Lys Lys Pro Met His Ala Thr Met Ser Arg Leu Ala Glu Arg Tyr
50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Arg Leu
            260                 265                 270

Asp Asp Gly Asp Glu Gly Glu Lys Lys Ser Met Ile Ala Val Leu Leu
        275                 280                 285

Thr Leu Gln Lys Thr Glu Pro Glu Val Tyr Thr Asp Asn Met Ile Thr
    290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
```

```
                   355                 360                 365
Arg Glu Thr Leu Arg Leu Tyr Pro Ala Ala Pro Met Leu Leu Pro His
        370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
            420                 425                 430

Cys Asp Gly Asn Leu Leu Met Pro Phe Gly Met Gly Arg Arg Arg Cys
                435                 440                 445

Pro Gly Glu Thr Leu Ala Leu Arg Thr Val Gly Leu Val Leu Gly Thr
        450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Pro Leu Glu
                485                 490                 495

Ala Met Cys Arg Pro Arg Asp Ala Met Gly Gly Val Leu Arg Glu Leu
            500                 505                 510
Val

<210> SEQ ID NO 6
<211> LENGTH: 1670
<212> TYPE: DNA
<213> ORGANISM: Artificial Sequence
<220> FEATURE:
<223> OTHER INFORMATION: Chemically Synthesized
<220> FEATURE:
<221> NAME/KEY: Cytochrome P450 ORF
<222> LOCATION: (123)..(1664)

<400> SEQUENCE: 6
ggatcctata aataggaagt tcatttcatt tggagaggaa acctcgagta tttttacaac      60
aattaccaac aacaacaaac aacaaacaac attacaatta ctatttacaa ttacagatct     120
ccatggataa cgcttatatt attgctattc tttctgttgc tattcttttc cttcttcatt     180
attatcttct tggaagagga aacggaggag ctgctagact ccaccaggga ccaccagctg     240
ttccaattct tggacatctt catcttgtta agaagccaat gcatgctact atgtctagac     300
ttgctgagag atatggacca gttttctctc ttagacttgg atctagaaga gctgttgttg     360
tttcttctcc aggatgcgct agagagtgct tcactgagca tgatgttact ttcgctaaca     420
gaccaagatt cgagtctcaa cttcttgttt ctttcaacgg agctgctctt gctactgctt     480
cttatggtgc tcattggaga aaccttagaa gaattgttgc tgttcaactt ctttctgctc     540
atagagttgg acttatgtct ggacttattg ctggagaggt tagagctatg gttagaagaa     600
tgtatagagc tgctgctgct tctccagctg gagctgctag aattcaactt aagagaagac     660
ttttcgaggt ttctctttct gttcttatgg agactattgc tcatactaag gctactagac     720
cagagactga tccagatact gatatgtctg ttgaggctca agagttcaag caagttgttg     780
atgagattat tccacatatt ggagctgcta acctttggga ttatcttcca gctcttagat     840
ggttcgatgt tttcggagtt agaagaagat tccttgctgc tgtttctaga agagatgctt     900
tccttagaag acttattgat gctgagagaa gaagacttga tgatggagat gagggagaga     960
agaagtctat gattgctgtt cttcttactc ttcaaaagac tgagccagag gtttatactg    1020
ataacatgat tactgctctt actgctaacc ttttcggagc tggaactgag actacttcta    1080
```

-continued

```
ctacttctga gtgggctatg tctcttcttc ttaaccatcc agatactctt aagaaggctc    1140
aagctgagat tgatgcttct gttggaaact ctagacttat tactgctgat gatgttacta    1200
gacttggata tcttcaatgc attgttagag agactcttag actttatcca gctgctccaa    1260
tgcttcttcc acatgagtct tctgctgatt gcaaggttgg aggatataac attccaagag    1320
gatctatgct tcttattaac gcttatgcta ttcatagaga tccagctgtt tgggaggagc    1380
cagagaagtt catgccagag agattcgagg atggaggatg cgatgaaaac cttcttatgc    1440
cattcggaat gggaagaaga agatgcccag agagactct  tgctcttaga actgttggac    1500
ttgttcttgg aactcttatt caatgcttcg attgggagag agttgatgga gttgaggttg    1560
atatgactga gggaggagga cttactattc caaaggttgt tccacttgag gctatgtgca    1620
gaccaagaga tgctatggga ggagttctta gagagcttgt ttaagagctc    1670
```

<210> SEQ ID NO 7
<211> LENGTH: 513
<212> TYPE: PRT
<213> ORGANISM: Zea mays

<400> SEQUENCE: 7

```
Met Asp Lys Ala Tyr Val Ala Ala Leu Ser Val Ala Phe Leu Phe Leu
1               5                   10                  15

Val His Tyr Leu Val Gly Arg Ala Ala Gly Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60

Arg His Gly Pro Val Phe Ser Leu Arg Met Gly Cys Arg Arg Ala Val
65                  70                  75                  80

Val Val Ser Ser Pro Glu Cys Ala Arg Ala Cys Phe Thr Glu His Asp
                85                  90                  95

Met Ser Phe Ala Asn Arg Pro Arg Phe Glu Ser Met Arg Leu Val Ser
            100                 105                 110

Phe Asp Gly Ala Met Leu Ser Val Ser Ser Tyr Gly Pro Tyr Trp Arg
        115                 120                 125

Thr Leu Arg Arg Val Ala Ala Val Gln Leu Leu Ser Ala His Arg Val
    130                 135                 140

Ala Cys Met Ser Pro Val Ile Cys Ala Glu Val Arg Ala Met Val Arg
145                 150                 155                 160

Arg Met Ala Arg Leu Ala Ala Gly Gly Ala Ala Arg Val Gln Leu Arg
                165                 170                 175

Arg Arg Leu Phe Glu Leu Ser Leu Gly Val Leu Met Glu Thr Ile Ala
            180                 185                 190

Arg Thr Lys Thr Ser Arg Ser Glu Ala Cys Ala Ala Asp Thr Asp Val
        195                 200                 205

Ser Pro Glu Ala Ser Glu Leu Thr Arg Ile Ser Glu Glu Ile Met Pro
    210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Asn Lys Leu Met Ala Ala Val Arg Trp
                245                 250                 255

Arg Asp Ala Phe Leu Arg Arg Leu Ile Asp Ala Glu Arg Arg Met
            260                 265                 270

Asp Gly Asp Gly Asp Gly Glu Lys Lys Ser Met Ile Ala Val Leu Leu
```

```
            275                 280                 285
Ser Leu Gln Lys Ser Glu Pro Glu Leu Tyr Thr Asp Thr Met Ile Met
290                 295                 300

Ala Leu Cys Gly Asp Leu Phe Gly Ala Gly Thr Glu Thr Thr Ser Val
305                 310                 315                 320

Thr Thr Glu Trp Ala Met Ser Leu Leu Leu Ser His Pro Glu Ala Leu
                325                 330                 335

Lys Lys Ala Gln Ala Glu Ile Asp Ala Val Val Gly Asn Ser Arg Arg
            340                 345                 350

Leu Ile Thr Ala Asp Asp Val Pro Arg Leu Gly Tyr Leu His Cys Val
        355                 360                 365

Ile Asn Glu Thr Leu Arg Met Tyr Pro Ala Ala Pro Leu Leu Leu Pro
370                 375                 380

His Glu Ser Ala Ala Asp Cys Lys Val Gly Gly Tyr Asp Val Pro Arg
385                 390                 395                 400

Gly Thr Leu Leu Ile Val Asn Ala Tyr Ala Ile His Arg Asp Pro Ala
                405                 410                 415

Val Trp Glu Asp Pro Gly Ser Phe Leu Pro Glu Arg Phe Glu Asp Gly
            420                 425                 430

Lys Ala Glu Gly Arg Leu Leu Met Pro Phe Gly Met Gly Arg Arg Lys
        435                 440                 445

Cys Pro Gly Glu Thr Leu Ala Leu Arg Thr Val Gly Leu Val Leu Ala
450                 455                 460

Thr Leu Leu Gln Cys Phe Asp Trp Asp Thr Val Asp Gly Ala Glu Val
465                 470                 475                 480

Asp Met Thr Glu Ser Gly Gly Leu Thr Met Pro Arg Ala Val Pro Leu
                485                 490                 495

Glu Ala Met Cys Lys Pro Arg Ala Ala Met Cys Asp Val Leu Arg Glu
            500                 505                 510

Leu

<210> SEQ ID NO 8
<211> LENGTH: 542
<212> TYPE: PRT
<213> ORGANISM: Zea mays

<400> SEQUENCE: 8

Met Ala His Asp Ala Arg Cys Cys Tyr Ala Asn Ala Thr Arg Leu Ser
1               5                   10                  15

Leu Thr Ser Met Met Asp Leu Ala Ala Tyr Ile Ala Ile Leu Ser Leu
            20                  25                  30

Val Phe Leu Phe Leu Leu Arg Arg Val His Gly Leu Ala Arg Arg Asp
        35                  40                  45

Gly Lys Ser Arg Ser Met Arg Arg Pro Pro Ser Pro Pro Gly Ala
    50                  55                  60

Val Pro Phe Leu Gly His Leu His Leu Ile Lys Lys Pro Phe His Ala
65                  70                  75                  80

Thr Leu Ser Gly Leu Ala Gln Arg His Gly Pro Val Phe Thr Leu Arg
                85                  90                  95

Leu Gly Ser Arg Asp Ala Ala Val Val Thr Ser Pro Ala Cys Ala Arg
            100                 105                 110

Glu Cys Phe Thr Glu His Asp Val Thr Phe Ala Asn Arg Ser Leu Leu
        115                 120                 125

Pro Ser Gln Arg Leu Val Thr Phe Asp Gly Ala Ala Leu Gly Thr Ala
    130                 135                 140
```

Ser Tyr Gly Pro Arg Trp Arg Asp Leu Arg Arg Val Ala Val Val Gln
145                 150                 155                 160

Leu Leu Ser Ala His Arg Val Gly Cys Met Ser Gly Val Ile Cys Gly
            165                 170                 175

Glu Val Arg Ala Met Val Arg Arg Leu His Arg Ala Ala Ala Ala Ser
        180                 185                 190

Ala Ala Ala Gly Ala Arg Ile Glu Leu Lys Arg Leu Phe Glu Leu
    195                 200                 205

Ser Leu Ser Val Leu Met Glu Ala Ile Ala Glu Thr Lys Ala Lys Arg
210                 215                 220

Arg Asp Pro Asp Pro Glu Pro Asp Ala Asp Gly Thr Thr Asp Met Ser
225                 230                 235                 240

Pro Glu Ala Gln Glu Phe Lys Arg Val Ile Asp Glu Val Phe Pro Tyr
                245                 250                 255

Val Ser Ser Val Leu Trp Asp Tyr Leu Pro Val Leu Arg Trp Phe Asp
            260                 265                 270

Val Ala Gly Val Arg Ser Arg Ile Leu Ala Ala Val Ser Arg Arg Asp
        275                 280                 285

Ala Phe Leu Arg Arg Leu Ile Asp Ala Glu Arg Arg Met Ala Asp
    290                 295                 300

Gly Val Cys Gly Glu Lys Lys Ser Leu Ile Ala Val Leu Leu Ala Leu
305                 310                 315                 320

Gln Lys Leu Glu Pro Glu Val Tyr Thr Asp Thr Val Ile Thr Ala Phe
                325                 330                 335

Cys Ser Asn Leu Phe Gly Ala Gly Thr Glu Thr Thr Ser Thr Thr Val
            340                 345                 350

Glu Trp Ala Met Ser Leu Leu Leu Asn Asn Pro Gly Thr Leu Glu Lys
        355                 360                 365

Ala Arg Ala Glu Ile Asp Ala Ala Val Gly His Ser Arg Leu Leu Asn
370                 375                 380

Ala Gly Asp Leu Pro Arg Leu Gly Tyr Leu Arg Cys Ile Ile Ala Glu
385                 390                 395                 400

Thr Leu Arg Leu Tyr Pro Ala Ala Pro Leu Leu Pro His Glu Ser
                405                 410                 415

Ser Ala Asp Cys Lys Val Gly Gly Tyr Asp Val Pro Arg Gly Thr Ala
            420                 425                 430

Leu Leu Val Asn Val Tyr Ala Ile His Arg Asp Pro Ala Val Trp Glu
        435                 440                 445

Glu Pro Gly Arg Phe Val Pro Glu Arg Phe Glu Gly Gly Lys Ala Glu
    450                 455                 460

Gly Leu Phe Val Ala Pro Phe Gly Met Gly Arg Arg Lys Cys Pro Gly
465                 470                 475                 480

Glu Arg Leu Ala Leu Gln Thr Val Gly Val Ala Leu Gly Ser Leu Ile
                485                 490                 495

Gln Cys Phe His Trp Asn Arg Val Asp Gly Val Glu Val Asp Met Ser
            500                 505                 510

Glu Gly Ser Gly Leu Thr Met Pro Lys Ala Val Pro Leu Glu Ala Leu
        515                 520                 525

Cys Thr Arg Glu Ala Met Tyr Asp Val Leu Gln Lys Ile
530                 535                 540

<210> SEQ ID NO 9
<211> LENGTH: 524
<212> TYPE: PRT

<213> ORGANISM: Catharanthus roseus

<400> SEQUENCE: 9

```
Met Glu Met Asp Met Asp Thr Ile Arg Lys Ala Ile Ala Ala Thr Ile
1               5                   10                  15

Phe Ala Leu Val Met Ala Trp Ala Trp Arg Val Leu Asp Trp Ala Trp
            20                  25                  30

Phe Thr Pro Lys Arg Ile Glu Lys Arg Leu Arg Gln Gln Gly Phe Arg
        35                  40                  45

Gly Asn Pro Tyr Arg Phe Leu Val Gly Asp Val Lys Glu Ser Gly Lys
    50                  55                  60

Met His Gln Glu Ala Leu Ser Lys Pro Met Glu Phe Asn Asn Asp Ile
65                  70                  75                  80

Val Pro Arg Leu Met Pro His Ile Asn His Thr Ile Asn Thr Tyr Gly
                85                  90                  95

Arg Asn Ser Phe Thr Trp Met Gly Arg Ile Pro Arg Ile His Val Met
            100                 105                 110

Glu Pro Glu Leu Ile Lys Glu Val Leu Thr His Ser Ser Lys Tyr Gln
        115                 120                 125

Lys Asn Phe Asp Val His Asn Pro Leu Val Lys Phe Leu Leu Thr Gly
    130                 135                 140

Val Gly Ser Phe Glu Gly Ala Lys Trp Ser Lys His Arg Arg Ile Ile
145                 150                 155                 160

Ser Pro Ala Phe Thr Leu Glu Lys Leu Lys Ser Met Leu Pro Ala Phe
                165                 170                 175

Ala Ile Cys Tyr His Asp Met Leu Thr Lys Trp Glu Lys Ile Ala Glu
            180                 185                 190

Lys Gln Gly Ser His Glu Val Asp Ile Phe Pro Thr Phe Asp Val Leu
        195                 200                 205

Thr Ser Asp Val Ile Ser Lys Val Ala Phe Gly Ser Thr Tyr Glu Glu
    210                 215                 220

Gly Gly Lys Ile Phe Arg Leu Leu Lys Glu Leu Met Asp Leu Thr Ile
225                 230                 235                 240

Asp Cys Met Arg Asp Val Tyr Ile Pro Gly Trp Ser Tyr Leu Pro Thr
                245                 250                 255

Lys Arg Asn Lys Arg Met Lys Glu Ile Asn Lys Glu Ile Thr Asp Met
            260                 265                 270

Leu Arg Phe Ile Ile Asn Lys Arg Met Lys Ala Leu Lys Ala Gly Glu
        275                 280                 285

Pro Gly Glu Asp Asp Leu Leu Gly Val Leu Leu Glu Ser Asn Ile Gln
    290                 295                 300

Glu Ile Gln Lys Gln Gly Asn Lys Lys Asp Gly Gly Met Ser Ile Asn
305                 310                 315                 320

Asp Val Ile Glu Glu Cys Lys Leu Phe Tyr Phe Ala Gly Gln Glu Thr
                325                 330                 335

Thr Gly Val Leu Leu Thr Trp Thr Thr Ile Leu Leu Ser Lys His Pro
            340                 345                 350

Glu Trp Gln Glu Arg Ala Arg Glu Glu Val Leu Gln Ala Phe Gly Lys
        355                 360                 365

Asn Lys Pro Glu Phe Glu Arg Leu Asn His Leu Lys Tyr Val Ser Met
    370                 375                 380

Ile Leu Tyr Glu Val Leu Arg Leu Tyr Pro Pro Val Ile Asp Leu Thr
385                 390                 395                 400

Lys Ile Val His Lys Asp Thr Lys Leu Gly Ser Tyr Thr Ile Pro Ala
```

```
                    405                 410                 415
Gly Thr Gln Val Met Leu Pro Thr Val Met Leu His Arg Glu Lys Ser
                420                 425                 430

Ile Trp Gly Glu Asp Ala Met Glu Phe Asn Pro Met Arg Phe Val Asp
            435                 440                 445

Gly Val Ala Asn Ala Thr Lys Asn Asn Val Thr Tyr Leu Pro Phe Ser
    450                 455                 460

Trp Gly Pro Arg Val Cys Leu Gly Gln Asn Phe Ala Leu Leu Gln Ala
465                 470                 475                 480

Lys Leu Gly Leu Ala Met Ile Leu Gln Arg Phe Lys Phe Asp Val Ala
                485                 490                 495

Pro Ser Tyr Val His Ala Pro Phe Thr Ile Leu Thr Val Gln Pro Gln
            500                 505                 510

Phe Gly Ser His Val Ile Tyr Lys Lys Leu Glu Ser
            515                 520

<210> SEQ ID NO 10
<211> LENGTH: 440
<212> TYPE: PRT
<213> ORGANISM: Avena sativa

<400> SEQUENCE: 10

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Ala Thr
                100                 105                 110

Ala Ser Ile Pro Ser Phe Ser Asp Ala Ala Arg Thr Phe Ala Ala
            115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
```

```
                   260                 265                 270
Asn Glu Pro Val His Gly Thr Lys Arg Arg Ser Gln Ile Gln Thr Tyr
            275                 280                 285

Leu Glu Tyr His Gly Gly Pro Gly Val Gln His Ile Ala Leu Ala Ser
        290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Gln Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
        435                 440

<210> SEQ ID NO 11
<211> LENGTH: 439
<212> TYPE: PRT
<213> ORGANISM: Avena sativa

<400> SEQUENCE: 11

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
```

```
                195                 200                 205
Tyr Gly Leu Thr Arg Phe Asp His Val Val Gly Asn Val Pro Glu Met
            210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Ser Gln Ile Gln Thr Tyr Leu
            275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 12
<211> LENGTH: 440
<212> TYPE: PRT
<213> ORGANISM: Avena sativa

<400> SEQUENCE: 12

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His Val Glu Leu
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Thr
                100                 105                 110

Ala Ser Ile Pro Ser Phe Ser Ala Asp Ala Ala Arg Thr Phe Ala Ala
            115                 120                 125

Ala His Gly Leu Ala Val Arg Ser Val Gly Val Arg Val Ala Asp Ala
```

```
             130                 135                 140
Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                    165                 170                 175

Tyr Gly Asp Val Val Leu Arg Phe Val Ser Tyr Pro Asp Glu Thr Asp
                    180                 185                 190

Leu Pro Phe Leu Pro Gly Phe Glu Arg Val Ser Ser Pro Gly Ala Val
                    195                 200                 205

Asp Tyr Gly Leu Thr Arg Phe Asp His Val Val Gly Asn Val Pro Glu
210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                    245                 250                 255

Asn Ser Val Val Leu Ala Asn Asn Ser Glu Ala Val Leu Leu Pro Leu
                    260                 265                 270

Asn Glu Pro Val His Gly Thr Lys Arg Arg Ser Gln Ile Gln Thr Tyr
                    275                 280                 285

Leu Glu Tyr His Gly Gly Pro Gly Val Gln His Ile Ala Leu Ala Ser
290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                    325                 330                 335

Val Arg Arg Ile Ala Gly Asp Val Leu Ser Glu Glu Gln Ile Lys Glu
                    340                 345                 350

Cys Gln Glu Leu Gly Val Leu Val Asp Arg Asp Gln Gly Val Leu
                    355                 360                 365

Leu Gln Ile Phe Thr Lys Pro Val Gly Asp Arg Pro Thr Phe Leu
370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                    405                 410                 415

Glu Leu Phe Lys Ser Ile Glu Asp Tyr Glu Lys Ser Leu Glu Val Lys
                    420                 425                 430

Gln Ser Val Val Ala Gln Lys Ser
                    435                 440

<210> SEQ ID NO 13
<211> LENGTH: 440
<212> TYPE: PRT
<213> ORGANISM: Avena sativa

<400> SEQUENCE: 13

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
                35                  40                  45

Trp Cys Ala Asp Ala Ala Ser Ala Ala Gly Arg Phe Ser Phe Ala Leu
            50                  55                  60

Gly Ala Pro Leu Ala Ala Arg Ser Asp Leu Ser Thr Gly Asn Ser Ala
```

```
            65                  70                  75                  80
His Ala Ser Leu Leu Arg Ser Gly Ala Leu Ala Phe Leu Phe Thr
                        85                  90                  95

Ala Pro Tyr Ala Pro Pro Gln Glu Ala Ala Asp Ala Ala Thr
                100                 105                 110

Ala Ser Ile Pro Ser Phe Ser Ala Asp Ala Ala Arg Thr Phe Ala Ala
            115                 120                 125

Ala His Gly Leu Ala Val Arg Ser Val Gly Val Arg Val Ala Asp Ala
        130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
                180                 185                 190

Leu Pro Phe Leu Pro Gly Phe Glu Arg Val Ser Ser Pro Gly Ala Val
                195                 200                 205

Asp Tyr Gly Leu Thr Arg Phe Asp His Val Val Gly Asn Val Pro Glu
210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
                260                 265                 270

Asn Glu Pro Val His Gly Thr Lys Arg Arg Ser Gln Ile Gln Thr Tyr
                275                 280                 285

Leu Glu Tyr His Gly Gly Pro Gly Val Gln His Ile Ala Leu Ala Ser
            290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Gln Ile Lys Glu
            340                 345                 350

Cys Gln Glu Leu Gly Val Leu Val Asp Arg Asp Gln Gly Val Leu
            355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
                420                 425                 430

Gln Ser Val Val Ala Gln Lys Ser
            435                 440

<210> SEQ ID NO 14
<211> LENGTH: 1323
<212> TYPE: DNA
<213> ORGANISM: Avena sativa

<400> SEQUENCE: 14
atgcctccaa caccagctac tgctactgga gctgctgctg ctgccgttac accagaacat    60
```

```
gctgcaaggt cattccctag agttgttcgc gttaaccota ggtctgacag attccctgtt      120
ctgtccttcc atcatgtgga gctttggtgt gctgatgcag ctagtgctgc tggtcgtttc      180
agctttgcac ttggagcacc acttgctgca agatctgatc tgtctacagg gaactcagca      240
catgcttctc tcctacttcg atctggagca ttagccttcc ttttaccgc tccttatgct       300 ccacctccac aagaagctgc aactgctgct gcaactgctt ccattccctc cttttcagca      360
gatgctgcaa gaacctttgc tgctgcacat ggacttgctg tcagatctgt tggagttagg      420
gttgctgatg cagctgaagc atttcgcgtt agtgttgctg gaggagcaag acctgctttt      480
gctccagcag atcttggtca cggatttgga cttgctgaag tggagctgta tggagatgtg      540
gttctgagat cgtgagcta tcctgacgaa actgacctac catttctccc aggattcgag       600
agggtttcaa gtccaggtgc agttgactac ggtttgactc gctttgacca cgttgttgga      660
aacgttccag aaatggctcc tgtcatcgac tacatgaagg gattccttgg tttccacgag      720
ttcgctgaat tcacagcaga ggatgttgga accacagaat ctggactgaa cagtgtggtt      780
ctagccaaca acagtgaagc tgttcttctg ccattgaacg agcctgttca tggaaccaag      840
agacgatctc agatccaaac ctacctcgaa taccatggtg gaccaggagt tcaacacatc      900
gcattggctt ctaacgatgt gcttcgaact ctcagggaaa tgagagccag aactccaatg      960
ggagggttcg aatttatggc tcctccacaa gccaagtact atgaaggagt ccgtagaatc     1020
gctggagatg tcttgtcaga ggaacagatc aaggagtgtc aagaactggg tgttctcgtt     1080
gatcgagacg atcaaggtgt gctactccag atcttcacca aaccagttgg tgatcgtccc     1140 actttttcc tcgaaatgat tcagcgaata ggatgcatgg agaaggatga agttgggcaa      1200
gagtaccaga aagtggatg tggtgggttt ggaaagggga acttttccga gttgttcaag     1260
tccatagagg actacgagaa gtcactggaa gtcaagcagt ctgtcgttgc tcagaagagc     1320
taa                                                                  1323

<210> SEQ ID NO 15
<211> LENGTH: 1320
<212> TYPE: DNA
<213> ORGANISM: Avena sativa

<400> SEQUENCE: 15
atgcctccaa caccagctac tgctactgga gctgctgctg ctgccgttac accagaacat       60
gctgcaaggt cattccctag agttgttcgc gttaacccta ggtctgacag attccctgtt      120
ctgtccttcc atcatgtgga gctttggtgt gctgatgcag ctagtgctgc tggtcgtttc      180
agctttgcac ttggagcacc acttgctgca agatctgatc tgtctacagg gaactcagca      240
catgcttctc tcctacttcg atctggagca ttagccttcc ttttaccgc tccttatgct       300 ccacctccac aagaagctgc aactgctgca actgcttcca ttccctcctt ttcagcagat      360
gctgcaagaa cctttgctgc tgcacatgga cttgctgtca gatctgttgg agttagggtt      420
gctgatgcag ctgaagcatt tcgcgttagt gttgctggag gagcaagacc tgcttttgct      480
ccagcagatc ttggtcacgg atttggactt gctgaagtgg agctgtatgg agatgtggtt      540
ctgagattcg tgagctatcc tgacgaaact gacctaccat ttctcccagg attcgagagg      600
gtttcaagtc caggtgcagt tgactacggt ttgactcgct ttgaccacgt tgttggaaac      660
gttccagaaa tggctcctgt catcgactac atgaagggat ccttggtttt ccacgagttc      720
gctgaattca cagcagagga tgttggaacc acagaatctg gactgaacag tgtggttcta      780
gccaacaaca gtgaagctgt tcttctgcca ttgaacgagc tgttcatgg aaccaagaga       840
```

```
cgatctcaga tccaaaccta cctcgaatac catggtggac caggagttca acacatcgca      900
ttggcttcta acgatgtgct tcgaactctc agggaaatga gagccagaac tccaatggga      960
gggttcgaat ttatggctcc tccacaagcc aagtactatg aaggagtccg tagaatcgct     1020
ggagatgtct tgtcagagga acagatcaag gagtgtcaag aactgggtgt tctcgttgat     1080
cgagacgatc aaggtgtgct actccagatc ttcaccaaac cagttggtga tcgtcccact     1140
tttttcctcg aaatgattca gcgaatagga tgcatggaga aggatgaagt tgggcaagag     1200
taccagaaag gtggatgtgg tgggtttgga aaggggaact tttccgagtt gttcaagtcc     1260
atagaggact acgagaagtc actggaagtc aagcagtctg tcgttgctca gaagagctaa     1320
```